US012773490B2

(12) United States Patent
Yannopoulos et al.

(10) Patent No.: US 12,773,490 B2
(45) Date of Patent: Oct. 27, 2026

(54) INTRAVENOUS DELIVERY OF LARGE VOLUMES OF GAS WITH HIGHLY PRESSURIZED SUPERSATURATED SOLUTION

(71) Applicants: Regents of the University of Minnesota, Minneapolis, MN (US); CARNEGIE INSTITUTION OF WASHINGTON, Washington, DC (US)

(72) Inventors: Demetris Yannopoulos, Edina, MN (US); Dionysios Foustoukos, Silver Spring, MD (US)

(73) Assignees: Regents of the University of Minnesota, Minneapolis, MN (US); CARNEGIE INSTITUTION OF WASHINGTON, Washington, DC (US)

( * ) Notice: Subject to any disclaimer, the term of this patent is extended or adjusted under 35 U.S.C. 154(b) by 502 days.

(21) Appl. No.: 18/548,814

(22) PCT Filed: Mar. 4, 2022

(86) PCT No.: PCT/US2022/070978
§ 371 (c)(1),
(2) Date: Sep. 1, 2023

(87) PCT Pub. No.: WO2022/187859
PCT Pub. Date: Sep. 9, 2022

(65) Prior Publication Data

US 2024/0148962 A1 May 9, 2024

Related U.S. Application Data

(60) Provisional application No. 63/200,429, filed on Mar. 5, 2021.

(51) Int. Cl.
*A61M 5/14* (2006.01)
*A61K 33/00* (2006.01)
*A61M 5/36* (2006.01)

(52) U.S. Cl.
CPC ............ *A61M 5/141* (2013.01); *A61K 33/00* (2013.01); *A61M 5/36* (2013.01);
(Continued)

(58) Field of Classification Search
CPC ........................ A61M 1/32; A61M 2202/0476
See application file for complete search history.

(56) References Cited

U.S. PATENT DOCUMENTS 5,407,426 A * 4/1995 Spears .................... C01B 13/02 62/51.1
6,555,059 B1 * 4/2003 Myrick .............. A61M 1/1698 604/4.01

(Continued)

FOREIGN PATENT DOCUMENTS

JP 2012213475 A 11/2012

OTHER PUBLICATIONS

Ahonen et al. et al., "Ion Mobility-Mass Spectrometry of Iodine Pentoxide-Iodic Acid Hybrid Cluster Anions in Dry and Humidified Atmospheres", The journal of physical chemistry letters, Apr. 2, 2019, 22 pp.

(Continued)

*Primary Examiner* — Laura A Bouchelle
(74) *Attorney, Agent, or Firm* — Shumaker & Sieffert, P.A.

(57) ABSTRACT

An example system includes a fluid delivery device configured to deliver gas nanobubbles to a target site of a patient from a solution comprising a fluid, supersaturated with a. gas, wherein the fluid delivery' device defines a flow channel configured to flow the solution through the flow channel
(Continued)

such that the gas in the supersaturated fluid forms gas nanobubbles as the solution flows through the flow channel towards the target site, and wherein the gas nanobubbles remain in the fluid at least until delivery' to the target site.

22 Claims, 13 Drawing Sheets

(52) U.S. Cl.
CPC .............. *A61M 2202/0007* (2013.01); *A61M 2202/0476* (2013.01); *A61M 2210/02* (2013.01); *A61M 2210/1042* (2013.01); *A61M 2210/12* (2013.01)

(56) References Cited

U.S. PATENT DOCUMENTS

| | | | | |
|---|---|---|---|---|
| 8,579,880 | B2 * | 11/2013 | Grady ..................... | A61M 1/32 604/113 |
| 2008/0262413 | A1 * | 10/2008 | Ladizinsky .......... | A61K 9/0026 604/20 |
| 2015/0133779 | A1 | 5/2015 | Yurek et al. | |
| 2019/0070370 | A1 | 3/2019 | Borden et al. | |

OTHER PUBLICATIONS

Attard, "The stability of nanobubbles", The European Physical Journal Special Topics, Apr. 2014, pp. 893-914.
Aufderheide et al., "Hyperventilation-induced hypotension during cardiopulmonary resuscitation", Circulation, vol. 109, No. 16, Apr. 2004, pp. 1960-1965.
Aufderheide et al., "Incomplete chest wall decompression: a clinical evaluation of CPR performance by EMS personnel and assessment of alternative manual chest compression-decompression techniques", Resuscitation, vol. 64, No. 3, Mar. 2005, pp. 353-362.
Aufderheide Md et al., "Comparative Effectiveness of Standard CPR versus Active Compression Decompression CPR with Augmentation of Negative Intrathoracic Pressure for Treatment of Out-of-Hospital Cardiac Arrest: Results from a Randomized Prospective Study", The Lancet, vol. 377, No. 9762, Jan. 22, 2011, pp. 301-311.
Awasthi et al., "Generalized Kinematics for Deformable Patient-Specific Soft Robots", IEEE Transactions on Robotics, 2010, 1 pp., (Applicant points out, in accordance with MPEP 609.04(a), that the year of publication, 2010, is sufficiently earlier than the effective U.S. filing date, so that the particular month of publication is not an issue.).
Babbs et al., "A dose-response curve for the negative bias pressure of an intrathoracic pressure regulator during CPR", Resuscitation, vol. 71, No. 3, Dec. 2006, 8 pp.
Bartos et al., "Improved Survival With Extracorporeal Cardiopulmonary Resuscitation Despite Progressive Metabolic Derangement Associated With Prolonged Resuscitation", Circulation, vol. 141, No. 11, Mar. 17, 2020, pp. 877-886.
Bartos et al., "Intracoronary Poloxamer 188 Prevents Reperfusion Injury in a Porcine Model of ST-Segment Elevation Myocardial Infarction", JACC: Basic to Translation Science, vol. 1, No. 4, Jun. 2016, pp. 224-234.
Bartos et al., "Refractory cardiac arrest: where extracorporeal cardiopulmonary resuscitation fits", Current opinion in critical care, Dec. 2020, pp. 596-602.
Bartos et al., "Role of epinephrine and extracorporeal membrane oxygenation in the management of ischemic refractory ventricular fibrillation: a randomized trial in pigs", Basic to Translational Science, Jun. 2017, pp. 244-253.
Bartos et al., "The Minnesota mobile extracorporeal cardiopulmonary resuscitation consortium for treatment of out-of-hospital refractory ventricular fibrillation: Program description, performance, and outcomes", EClinicalMedicine, Dec. 2020, 10 pp.
Bhushan et al., "AFM characterization of nanobubble formation and slip condition in oxygenated and electrokinetically altered fluids", Journal of colloid and interface science, Feb. 15, 2013, pp. 105-116.
Bohach et al., "Modeling and Optimization Study of a Tightly Integrated Rotary Electric Motor-Hydraulic Pump", Fluid Power Systems Technology, Oct. 2019, 10 pp.
Bohach Md et al., "Impact of Dynamics on the Losses at Radial Ball Piston Pump Interfaces", Fluid Power Systems Technology, American Society of Mechanical Engineers, vol. 83754, Sep. 2020, 12 pp.
Cavalli et al., "Ultrasound-mediated oxygen delivery from chitosan nanobubbles", International Journal of Pharmaceutics, vol. 378, No. 1-2, Aug. 2009, pp. 215-217.
Christmas et al., "Equations for O2 and CO2 solubilities in saline and plasma: combining temperature and density dependences", Journal of applied physiology, May 2017, pp. 1131-1320.
Chung et al., "Size distribution of air bubbles entering the brain during cardiac surgery", PLOS, Apr. 2, 2015, 11 pp.
Couto et al., "Micro-bubble size distribution measurements by laser diffraction technique", Minerals Engineering, Mar. 2009, pp. 330-335.
Debaty Md et al., "Sodium Nitroprusside-enhanced Cardiopulmonary Resuscitation Facilitates Intra-Arrest Therapeutic Hypothermia in a Porcine Model of Prolonged Ventricular Fibrillation", Critical care medicine, Apr. 2015, 15 pp.
Dunford et al., "A study of decompression sickness using recorded depth-time profiles", Undersea & Hyperbaric Medicine, vol. 47, No. 1, Jan. 2020, 16 pp.
Feshitan et al., "Systemic oxygen delivery by peritoneal perfusion of oxygen microbubbles", Biomaterials, Mar. 2014, pp. 2600-2606.
Fredericks et al., "Quantification of drifting droplets in sprays experiencing crosswind shear via digital image analysis techniques", 2020 ASABE Annual International Virtual Meeting. American Society of Agricultural and Biological Engineers, Jul. 2020, 8 pp.
Fulbright et al., "Automated Design and Analysis of a Variable Displacement Linkage Motor", Fluid Power Systems Technology, American Society of Mechanical Engineers, vol. 59339, Oct. 2019, 11 pp.
Gandhi et al., "Learning to Predict Coronary Perfusion Pressure During Cardiopulmonary Resuscitation", Dynamic Systems and Control Conference, American Society of Mechanical Engineers., Sep. 2018, 12 pp.
Ghaani et al., "Massive generation of metastable bulk nanobubbles in water by external electric fields", vol. 6, No. 14, Apr. 3, 2020, 7 pp.
Ghosh et al. et al., "Fragmentation and film growth in supersonic nanoaggregate aerosol deposition", AIChE Journal 66.4, vol. 66, No. 4, Nov. 20, 2019, 12 pp.
Goldman et al., "An explicitly multi-component arterial gas embolus dissolves much more slowly than its one-component approximation", Mathematical Biosciences, Aug. 2020, 13 pp.
Gopalakrishnan et al., "Determination of the Transition Regime Collision Kernelfrom Mean First Passage Times", Aerosol Science and Technology, vol. 45, No. 12, Dec. 2011, pp. 1499-1509.
Hogan Jr et al., "Sampling methodologies and dosage assessment techniques for submicrometre and ultrafine virus aerosol particles", Journal of applied microbiology, Dec. 2005, pp. 1422-1434.
International Preliminary Report on Patentability from International Application No. PCT/US2022/070978 dated Aug. 29, 2023, 10 pp.
International Search Report and Written Opinion of International Application No. PCT/US2022/070978 dated Jun. 30, 2022, 15 pp.
Kabalnov et al., "Dissolution of multicomponent microbubbles in the bloodstream: 1. Theory", Ultrasound in Medicine & Biology, vol. 24, No. 5, Jun. 1998, pp. 739-749.
Kavanagh, "Anemia, hypoxia and hypercapnia thresholds. Lessons from physiological limits in critically ill patients", Canadian Journal of Anesthesia, May 1, 1999, pp. 145-155.
Kettleson et al., "Airborne virus capture and inactivation by an electrostatic particle collector", Environmental science & technology, Aug. 2009, pp. 5940-5946.
Kheir et al., "Oxygen gas-filled microparticles provide intravenous oxygen delivery", Science translational medicine, Jun. 27, 2012, 10 pp.

(56) References Cited

OTHER PUBLICATIONS

Koynov et al., "Characterization of the localized hydrodynamic shear forces and dissolved oxygen distribution in sparged bioreactors", Biotechnology and bioengineering, Jun. 2007, pp. 317-331.
Kumar et al., "Automated droplet size distribution measurements using digital inline holography", Journal of Aerosol Science, vol. 137, Nov. 2019, 17 pp.
Li et al., "Design, Dynamic Modeling, and Experimental Validation of A Novel Alternating Flow Variable Displacement Hydraulic Pump", IEEE/ASME Transactions on Mechatronics, Mar. 2019, pp. 1294-1305.
Li et al., "Dynamic Model of a Novel Alternating Flow (AF) Hydraulic Pump", Fluid Power Systems Technology, American Society of Mechanical Engineers, vol. 58332, Oct. 2017, 9 pp.
Li et al., "Mass, momentum, and energy transfer in supersonic aerosol deposition processes", International Journal of Heat and Mass Transfer, Feb. 2019, 33 pp.
Li et al., "State of oxygen molecules in aqueous supersaturated solutions", The Journal of Physical Chemistry B, vol. 123, No. 18, Mar. 15, 2019, pp. 4025-4043.
Li et al., "Understanding vapor nucleation on the molecular level: A review", Journal of Aerosol Science, vol. 153, Mar. 2021, 45 pp.
Link et al., "Part 7: adult advanced cardiovascular life support: 2015 American Heart Association guidelines update for cardiopulmonary resuscitation and emergency cardiovascular care", Circulation, vol. 132, No. 18, Nov. 2015, p. 277.
Ljunggren et al., "The lifetime of a colloid-sized gas bubble in water and the cause of the hydrophobic attraction", Colloids and Surfaces A: Physicochemical and Engineering Aspects, vol. 129-130, No. 30, Nov. 30, 1997, pp. 151-155.
Lotfi et al., "SCAI expert consensus statement on out of hospital cardiac arrest", Catheterization and cardiovascular interventions: official journal of the Society for Cardiac Angiography & Interventions, vol. 94, No. 4, Oct. 2020, pp. 844-861.
Lurie MD et al., "Comparison of a 10-breaths-per-minute versus a 2-breaths-per-minute strategy during cardiopulmonary resuscitation in a porcine model of cardiac arrest", Respiratory care, vol. 53, No. 7, Jul. 2008, pp. 862-870.
Marino MD et al., "Spontaneous breathing through an inspiratory impedance threshold device augments cardiac index and stroke vol. index in a pediatric porcine model of hemorrhagic hypovolemia", Critical care medicine, vol. 32, No. 9, Sep. 2004, pp. 398-405.
Matsuki et al., "Blood oxygenation using microbubble suspensions", European Biophysics Journal, Jun. 2012, pp. 571-578.
Matsuki et al., "Oxygen supersaturated fluid using fine micro/nanobubbles", International Journal of Nanomedicine, Sep. 23, 2014, pp. 4495-4505.
Mccarthy et al., "Air Embolism: Diagnosis, Clinical Management and Outcomes", Diagnostics, vol. 7, No. 1, Jan. 17, 2017, 10 pp.
Murphy et al., "Deaths: final data for 2010", National Vital Statistics Report, vol. 61, No. 4, May 8, 2013, 118 pp.
Namura et al., "Quasi-stokeslet induced by thermoplasmonic Marangoni effect around a water vapor microbubble", Scientific reports, vol. 7, No. 1, Mar. 2017, 8 pp.
Nayak et al., "Permissive hypercapnia: Is there any upper limit?", Indian Journal of Critical Care Medicine, Dec. 2015, pp. 56-57.
Nishanth et al., "Nishanth FNU, Bohach G, Nahin MM, Ven JVd and Severson EL. Design of an axial flux machine with an integrated hydraulic pump for off-highway vehicle electrification. 2020 IEEE Energy Conversion Congress and Exposition (ECCE). 2020:1772-1779.", 2020 IEEE Energy Conversion Congress and Exposition (ECCE), Oct. 11, 2020, 8 pp.
O'Connor et al., "Part 10: Acute Coronary Syndromes 2010 American Heart Association Guidelines for Cardiopulmonary Resuscitation and Emergency Cardiovascular Care", vol. 122, No. 18, Nov. 2010, pp. S787-S817.
Ostwald, "Studien über die Bildung und Umwandlung fester Körper", February 1897, pp. 289-330.
Parkinson et al., "The terminal rise velocity of 10-100 μm diameter bubbles in water", Journal of Colloid and Interface Science, vol. 322, No. 1, Jun. 1, 2008, pp. 168-172.
Petersson et al., "Gas exchange and ventilation-perfusion relationships in the lung", European Respiratory Journal, Oct. 2014, pp. 1023-1041.
Piya et al., "Numerical Modeling of Liquid Piston Gas Compression", ASME International Mechanical Engineering Congress and Exposition, Nov. 2009, 11 pp.
Pourkarimi et al., "Effective parameters on generation of nanobubbles by cavitation method for froth flotation applications", Physicochemical Problems of Mineral Processing, Dec. 2016, pp. 920-942.
Presson Jr et al., "Effect of ventilation with soluble and diffusible gases on the size of air emboli", Journal of Applied Physiology, Mar. 1991, pp. 1068-1074.
Presson Jr et al., "Fate of air emboli in the pulmonary circulation", Journal of applied physiology, Nov. 1989, pp. 1898-1902.
Qiao et al., "Greater than 3-Log Reduction in Viable Coronavirus Aerosol Concentration in Ducted Ultraviolet-C (UV-C) Systems", Environmental science & technology, Dec. 2020, pp. 4174-4782.
Ripeckyj et al., "Sodium Nitroprusside-Enhanced Cardiopulmonary Resuscitation Improves Blood Flow by Pulmonary Vasodilation Leading to Higher Oxygen Requirements", J Am Coll Cardiol Basic Trans Science, Feb. 2020, pp. 183-192.
Sayadi et al., "Topical oxygen therapy & micro/nanobubbles: a new modality for tissue oxygen delivery", International wound journal, vol. 15, No. 3, Jun. 2018, pp. 363-374.
Schellart et al., "Relationships between plasma lipids, proteins, surface tension and post-dive bubbles", Undersea and Hyperbaric Medicine, vol. 42, No. 2, Feb. 13, 2015, 9 pp.
Schultz et al., "Sodium nitroprusside enhanced cardiopulmonary resuscitation prevents post-resuscitation left ventricular dysfunction and improves 24-hour survival and neurological function in a porcine model of prolonged untreated ventricular fibrillation", Resuscitation, Dec. 2011, 16 pp.
Schultz MD et al., "Sodium nitroprusside enhanced cardiopulmonary resuscitation (SNPeCPR) improves vital organ perfusion pressures and carotid blood flow in a porcine model of cardiac arrest", Resuscitation, Mar. 2012, pp. 374-377.
Schultz MD et al., "Sodium nitroprusside-enhanced cardiopulmonary resuscitation improves resuscitation rates after prolonged untreated cardiac arrest in two porcine models", Critical care medicine, vol. 39, No. 12, Dec. 2011, pp. 2705-2710.
Segal et al., "Impairment of carotid artery blood flow by supraglottic airway use in a swine model of cardiac arrest", Resuscitation, vol. 83, No. 8, Aug. 2012, pp. 1025-1030.
Segal et al., "Improving microcirculation with therapeutic intrathoracic pressure regulation in a porcine model of hemorrhage", Resuscitation, Dec. 2011, 14 pp.
Segal et al., "Ischemic postconditioning at the initiation of cardiopulmonary resuscitation facilitates functional cardiac and cerebral recovery after prolonged untreated ventricular fibrillation", Resuscitation, vol. 83, No. 11, Nov. 2012, pp. 1397-1403.
Siela et al., "Oxygen Requirements for Acutely and Critically Ill Patients", Critical Care Nurse, vol. 37, No. 4, Aug. 2017, pp. 58-70.
Sigurdsson MD et al., "Cardiorespiratory interactions and blood flow generation during cardiac arrest and other states of low blood flow", Current Opinion in Critical Care, Jun. 2003, pp. 183-188.
Singh et al., "Intravenous Injection of Oxygen: Under Normal Atmospheric Pressure", The Lancet, vol. 235, No. 6090, May 18, 1940, pp. 922-923.
Sullivan et al., "Topological Synthesis and Integrated Kinematic-Structural Dimensional Optimization of a Ten-Bar Linkage for a Hydraulic Rescue Spreader", International Design Engineering Technical Conferences and Computers and Information in Engineering Conference, American Society of Mechanical Engineers, vol. 55935, Aug. 2013, 16 pp.
Tauber et al., "Heterogeneous nucleation onto monoatomic ions: Support for the Kelvin-Thomson theory", ChemPhysChem, vol. 19, No. 22, Nov. 19, 2018, pp. 3144-3149.
Thajudeen et al., "The Collision Rate of Nonspherical Particles and Aggregatesfor all Diffusive Knudsen Numbers", Aerosol Science and Technology, vol. 46, No. 11, Nov. 2012, pp. 1174-1186.

(56) References Cited

OTHER PUBLICATIONS

Thomas et al., "Differential heat and mass transfer rate influences on the activation efficiency of laminar flow condensation particle counters", International Journal of Heat and Mass Transfer, vol. 127, Dec. 2018, pp. 740-750.
Tian et al., "Modeling and Experimental Studies on the Absorption of Entrained Gas and the Influence on Fluid Compressibility", Journal of Fluids Engineering, vol. 139, No. 10, Jul. 2017, 8 pp.
Tiruvoipati et al., "Association of Hypercapnia and Hypercapnic Acidosis With Clinical Outcomes in Mechanically Ventilated Patients With Cerebral Injury", JAMA neurology, vol. 75, No. 7, Jul. 2018, pp. 818-826.
Torres et al., "Tissue oxygenation and microvascular hemodynamics in experimental arterial gas embolism", Undersea & Hyperbaric Medicine, vol. 38, No. 6, Nov. 2011, p. 537.
Tu et al., "Design, Modeling, and Validation of a High-Speed Rotary Pulse-Width-Modulation On/Off Hydraulic Valve", Journal of dynamic systems, measurement, and control, Nov. 2012, 13 pp.
Tunnicliffe et al., "The intravenous injection of oxygen gas as a therapeutic measure", The Lancet, Aug. 1916, pp. 321-323.
Van De Ven et al., "Development of a hydro-mechanical hydraulic hybrid drive train with independent wheel torque control for an urban passenger vehicle", Proceedings of the national conference on fluid power, vol. 51, Mar. 12, 2008, 11 pp.
Voicu et al., "Synchronized pulsatile flow with low systolic output from veno-arterial extracorporeal membrane oxygenation improves myocardial recovery after experimental cardiac arrest in pigs", Artificial Organs, Jun. 2018, pp. 597-604.
Walke et al., "Experimental study on comparison of rising velocity of bubbles and light weight particles in the bubble column", International Journal of Chemical Engineering and Applications, vol. 3, No. 1, Feb. 2012, pp. 25-30.
Wang et al., "Generation and Stability of Size-Adjustable Bulk Nanobubbles Based on Periodic Pressure Change", Scientifc Reports, Feb. 2019, 9 pp.
Yang et al., "Condensation and dissociation rates for gas phase metal clusters from molecular dynamics trajectory calculations", The Journal of chemical physics, vol. 148, No. 16, Apr. 28, 2018, 12 pp.
Yang et al., "Excess thermal energy and latent heat in nanocluster collisional growth", The Journal of Chemical Physics, vol. 151, No. 22, Dec. 14, 2019, 12 pp.
Yang, "Dynamics of gas bubbles in whole blood and plasma", Journal of biomechanics, Mar. 1971, pp. 119-125.
Yannopoulos et al., "Advanced reperfusion strategies for patients with out-of-hospital cardiac arrest and refractory ventricular fibrillation (ARREST): a phase 2, single centre, open-label, randomised controlled trial", The Lancet, Dec. 5, 2020, pp. 1807-1816.
Yannopoulos et al., "Effects of incomplete chest wall decompression during cardiopulmonary resuscitation on coronary and cerebral perfusion pressures in a porcine model of cardiac arrest", Resuscitation, vol. 64, No. 3, Mar. 2005, pp. 363-372.
Yannopoulos et al., "Hemodynamic and respiratory effects of negative tracheal pressure during CPR in pigs", Resuscitation, vol. 69, No. 3, Jun. 2006, pp. 487-494.
Yannopoulos et al., "Intrathoracic pressure regulation improves vital organ perfusion pressures in normovolemic and hypovolemic pigs", Resuscitation, vol. 70, No. 3, Sep. 2006, pp. 445-453.
Yannopoulos et al., "No assisted ventilation cardiopulmonary resuscitation and 24-hour neurological outcomes in a porcine model of cardiac arrest", Critical care medicine, vol. 38, No. 1, Jan. 2010, pp. 254-260.
Yannopoulos et al., "Quality of CPR: An important effect modifier in cardiac arrest clinical outcomes and intervention effectiveness trials", Resuscitation, vol. 94, Sep. 2015, pp. 106-113.
Yannopoulos et al., "Reducing ventilation frequency combined with an inspiratory impedance device improves CPR efficiency in swine model of cardiac arrest", Resuscitation, vol. 61, No. 1, Apr. 2004, pp. 75-82.
Yannopoulos MD et al., "Clinical and hemodynamic comparison of 15: 2 and 30: 2 compression-to-ventilation ratios for cardiopulmonary resuscitation", Critical care medicine, vol. 34, No. 5, May 2006, pp. 1444-1449.
Yannopoulos MD et al., "Controlled pauses at the initiation of sodium nitroprusside-enhanced cardiopulmonary resuscitation facilitate neurological and cardiac recovery after 15 mins of untreated ventricular fibrillation", Critical care, vol. 40, No. 5, May 2012, pp. 1562-1569.
Yannopoulos MD et al., "Coronary Artery Disease in Patients With Out-of-Hospital Refractory Ventricular Fibrillation Cardiac Arrest", Journal of the American College of Cardiology, Aug. 29, 2017, pp. 1109-1117.
Yannopoulos MD et al., "Flow or no flow: That is the question!", Critical care medicine, May 2008, pp. 1677-1678.
Yannopoulos MD et al., "Intra-Cardiopulmonary Resuscitation Hypothermia With and Without Volume Loading in an Ischemic Model of Cardiac Arrest", Circulation, Oct. 2009, pp. 1426-1435.
Yannopoulos MD et al., "Rationale and methods of the Advanced R2Eperfusion STrategies for Refractory Cardiac Arrest (ARREST) trial", American Heart Journal, vol. 229, Nov. 2020, pp. 29-39.
Yannopoulos MD et al., "Reducing ventilation frequency during cardiopulmonary resuscitation in a porcine model of cardiac arrest", Respiratory care, vol. 50, No. 5, May 2005, pp. 628-635.
Yannopoulos MD et al., "Sodium nitroprusside enhanced cardiopulmonary resuscitation improves short term survival in a porcine model of ischemic refractory ventricular fibrillation", Resuscitation, Jan. 2017, 15 pp.
Yannopoulos MD et al., "The Evolving Role of the Cardiac Catheterization Laboratory in the Management of Patients With Out-of-Hospital Cardiac Arrest: A Scientific Statement From the American Heart Association", Circulation, vol. 139, No. 12, Mar. 2019, pp. e530-e552.
Zimmerman et al., "Microbubble generation", Recent patents on engineering, Jan. 2008, 13 pp.

* cited by examiner

High flow
6 ml /second of
O2SSS
expansion in
saline bath.

Low flow
1 ml /second
of O2SSS
expansion in
saline bath

INTRAVENOUS DELIVERY OF LARGE VOLUMES OF GAS WITH HIGHLY PRESSURIZED SUPERSATURATED SOLUTION

This application is a national stage entry of International Patent Application No. PCT/US2022/070978, filed Mar. 4, 2022, which claims priority to U.S. Provisional Patent Application No. 63/200,429, filed Mar. 5, 2021, the entire contents of application nos. PCT/US2022/070978 and 63/200,429 are incorporated herein by reference.

TECHNICAL FIELD

The invention relates to intravenous gas delivery.

BACKGROUND

The human body depends on intact lung function and appropriate ventilation/perfusion (V/Q) matching to exchange gasses and receive oxygen. Whenever the lung function or V/Q matching fails, the ability of the body to adjust is limited and leads to acute shock, blood hypoxemia, and tissue hypoxia that, if not reversed swiftly, in turn lead to organ damage or death. A large number of medical conditions can lead to a decrease in oxygen delivery, with failure of the cardiorespiratory system and necessity of intubation to counteract hypoxemia.

SUMMARY

In general, direct intravenous delivery of gasses has been discouraged because of the risk of air embolism. However, the ability to deliver high-content oxygen solutions intravenously may ameliorate injury, improve tissue hypoxia, and delay failure of the cardiorespiratory system long enough for definitive interventions and/or eliminate the need for invasive interventions such as intubations. Under normal pressure and temperatures compatible with intravenous injection (e.g., 4-37 degrees Celsius (° C.)), 1 liter (L) of saline contains 25-40 milliliters (mL) of oxygen ($O_2$) in solution.

Oxygen in a saline solution may be more readily absorbed if the oxygen is in the form of nanobubbles (e.g., bubbles having diameters less than about 1000 nanometers (nm), less than about 500 nm, or between about 5 and 100 nm). The creation of nanobubbles with high energy ultrasonication of the oxygen-infused solution under the same normotensive conditions (e.g., normal intravascular or intra-patient pressures) can raise the dissolved content from 25-40 ml of $O_2$ per 1 L of saline to about 55-80 ml of $O_2$ per 1 L of saline. The minute oxygen requirements of a human are 3 ml per kilogram (kg) per minute (min) or 200-300 ml of $O_2$/min. As such, the above solutions may not be adequate for emergencies requiring significant oxygen delivery because the required saline flow rates may be prohibitive.

Oxygen content dissolved into saline (e.g., 0.9% sodium chloride (NaCl)) is linearly associated with pressure and the slope is determined by the temperature with lower temperatures having higher value slopes. This disclosure describes systems configured to intravenously deliver a pressurized saline solution infused with a large volume of oxygen. By using high pressure, adequate volumes of oxygen (or some other gas, such as nitrous oxide) may be dissolved in a saline solution (or some other solution) to provide a clinically relevant therapy that can sustain metabolic requirements of a patient while substantially decreasing the risk of embolisms.

The techniques of this disclosure are based on the principle that when a highly pressurized solution is released under constant pressure (or the pressure is allowed to decay in a controlled fashion) through a nozzle (e.g. a Venturi tube) or capillary that controls the size of the bubble formation and/or flow rates, nanobubbles of the gas may form. These nanobubbles may be delivered (in the form of a "mist") into a venous system or any other aqueous environment for mixing with venous blood. For example, the nanobubbles may be delivered to the vasculature of a patient, the gastrointestinal (GI) track for absorption of the gaseous solution with direct effect in the GI track and circulation, subcutaneously for absorption, intraosseously for immediate absorption in the venous system, etc. The generation of nanobubbles can happen either before entering into the blood stream (e.g., within a portion of the delivery device) or inside the blood stream.

In this way, a supersaturated solution can act as the vehicle for the intravenous delivery of a "mist" of nanobubbles controlled by an appropriate nozzle and/or capillary configuration. For example, a system in accordance with techniques described herein may deliver a high-pressure, high-O content, supersaturated solution ($O_2$SSS) using an appropriate nozzle configuration that causes the generation of a nanobubble mist that is then delivered into the patient's bloodstream. The presence of venous, unsaturated hemoglobin may act as an absorption sink for the delivered mist of oxygen nanobubbles. A rate of mixing may be selected to ensure safe delivery (e.g., decreased bubble formations) of the solution to the patient (e.g., through the process of immediate $O_2$ uptake, which may be a consequence of oxygen being in the form of nanobubbles).

The systems and techniques of this disclosure can provide enormous benefits for individuals and public health in general. For example, applying these techniques may increase the likelihood of survival and quality of life for patients with cardiac arrest, hypoxic respiratory failure, cardiogenic shock, septic shock, and other emergencies requiring stabilization, intubation, and anesthesia. Other indication for use of the nanobubble mixture may include hyperbaric oxygen treatment (e.g., to treat sick scuba divers and people suffering from carbon monoxide poisoning, including firefighters and miners). Other indications for use of the nanobubble mixture may include treatment of burns, bone disease, carbon monoxide poisoning, cyanide poisoning, crush injuries, gas gangrene (i.e., a form of gangrene in which gas collects in tissues), decompression sickness, acute or traumatic inadequate blood flow in the arteries, compromised skin grafts and flaps, infection in a bone (e.g., osteomyelitis), delayed radiation injury, flesh-eating disease (also called necrotizing soft tissue infection) air or gas bubble trapped in a blood vessel (air or gas embolism), chronic infection called actinomycosis, diabetic wounds that are not healing properly, ischemic bowel disease, etc. The method of delivery can be intravenous, with local injection, subcutaneous or bathing in a solution.

Thus, this disclosure describes the fusion of physiology-based therapies with advances in gas solution physics to create a clinically relevant oxygen delivery system that can improve patient-related outcomes in a number of hypoxemic acute states and ultimately improve survival. The successful understanding of the physiological and physical components of this $O_2$SSS/blood interaction may open countless doors for innovative therapies.

In one example, a system includes: a fluid delivery device configured to deliver gas nanobubbles to a target site of a patient from a solution comprising a fluid supersaturated with a gas, wherein the fluid delivery device defines a flow channel configured to flow the solution through the flow channel such that the gas in the supersaturated fluid forms gas nanobubbles as the solution flows through the flow channel towards the target site, and wherein the gas nanobubbles remain in the fluid at least until delivery to the target site.

In one example, a method includes: delivering, via a fluid delivery device, gas nanobubbles to a target site of a patient from a solution comprising a fluid supersaturated with a gas, wherein the fluid delivery device defines a flow channel configured to flow the solution through the flow channel such that the gas in the supersaturated fluid forms gas nanobubbles as the solution flows through the flow channel towards the target site, and wherein the gas nanobubbles remain in the fluid at least until delivery to the target site.

The details of one or more aspects of the disclosure are set forth in the accompanying drawings and the description below. Other features, objects, and advantages of the techniques described in this disclosure will be apparent from the description, drawings, and claims.

DETAILED DESCRIPTION

Figure 1:
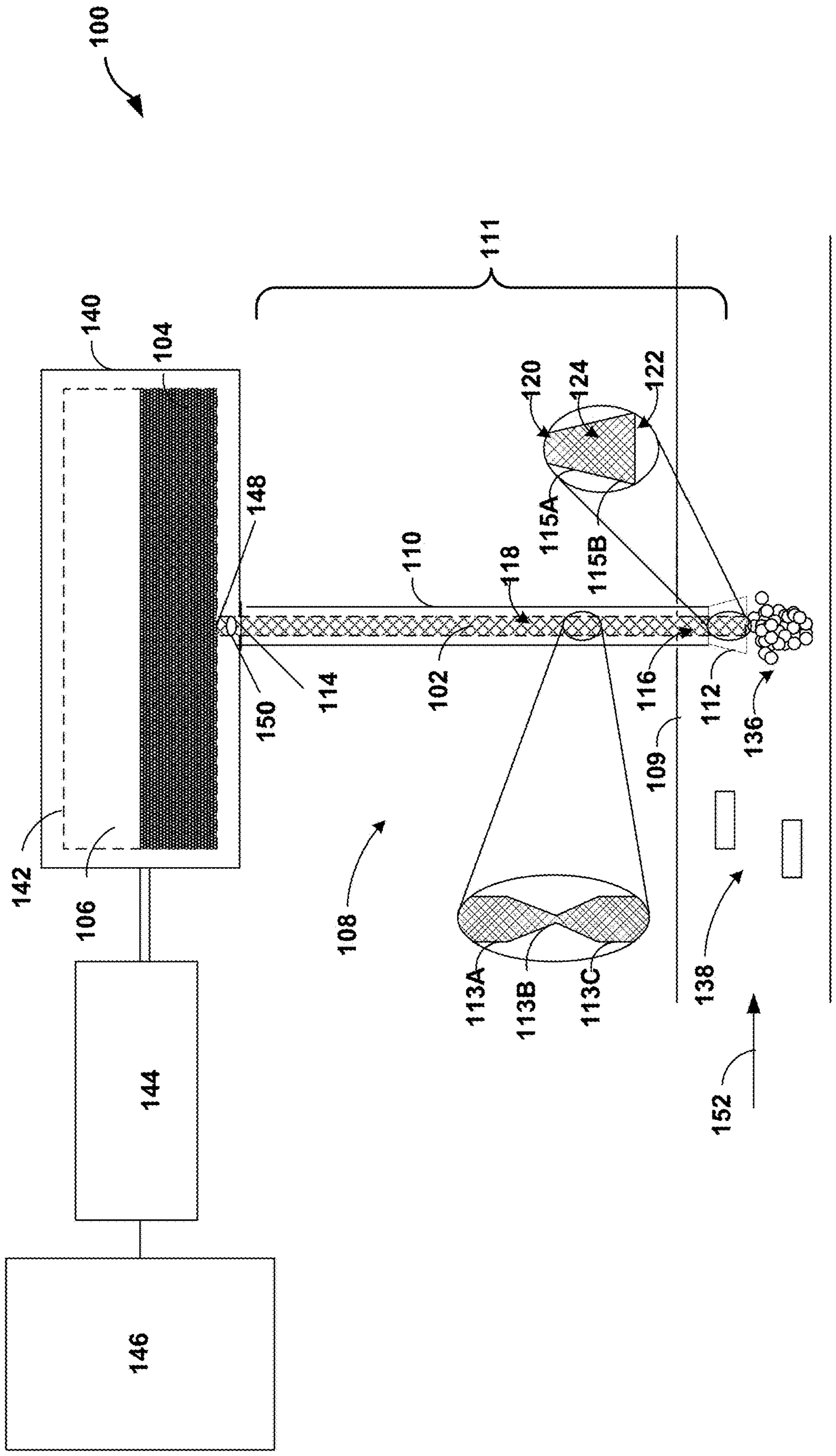
FIG. 1 is a conceptual diagram of an example system configured to intravenously deliver a solution of a fluid infused with a large volume of a gas, in accordance with one or more aspects of this disclosure.

The human body depends on intact lung function and appropriate ventilation/perfusion (V/Q) matching to exchange gasses and receive oxygen. Whenever the lung function or V/Q matching fails, the ability of the body to adjust is limited and leads to acute shock, blood hypoxemia, and tissue hypoxia that, if not reversed swiftly, leads to organ damage or death. Many medical conditions can lead to a decrease in oxygen delivery, resulting in failure of the cardiorespiratory system and necessitating intubation to counteract hypoxemia. In emergencies, carbon dioxide ($CO_2$) retention is less of a problem because the transfer coefficient in the lung is higher for $CO_2$ than for oxygen ($O_2$). The human body, especially the brain, cannot tolerate hypoxia.

In general, direct intravenous delivery of gasses has been discouraged because of the risk of air embolism. However, the ability to deliver high-content oxygen solutions intravenously may ameliorate injury, improve tissue hypoxia, and delay failure of the cardiorespiratory system long enough for definitive interventions and/or eliminate the need for invasive interventions such as intubations. Under normal pressure and temperatures compatible with intravenous injection (4-37 degrees Celsius (° C.)), 1 liter (L) of saline contains 25-40 milliliters (mL) of oxygen ($O_2$) in solution.

Oxygen in a saline solution may be more readily absorbed if the oxygen is in the form of nanobubbles (e.g., bubbles having diameters less than about 1000 nm, less than about 500 nm, or between about 5 nm and 100 nm). The creation of nanobubbles with high energy ultrasonication of the oxygen-infused solution under the same normotensive conditions can raise the dissolved content from 25-40 ml of $O_2$ per 1 L of saline to about 55-80 ml of $O_2$ per 1 L of saline. The minute oxygen requirements of a human are 3 ml per kilogram (kg) per minute (min) or 200-300 ml of $O_2$/min. As such, the above solutions may not be adequate for emergencies requiring significant oxygen delivery because the required saline flow rates may be prohibitive.

Oxygen content dissolved into saline (0.9% sodium chloride (NaCl)) is linearly associated with pressure and the slope is determined by the temperature with lower temperatures having higher value slopes. This disclosure describes systems configured to intravenously deliver a pressurized saline solution infused with a large volume of oxygen. By using high pressure, adequate volumes of oxygen (or some other gas, such as nitrous oxide) may be dissolved in a saline solution (or some other solution) to provide a clinically relevant therapy that can sustain metabolic requirements of a patient while substantially reducing the risk of embolism during direct intravenous delivery of gasses.

As described herein, methods, systems, and devices may safely infuse oxygen (and other gasses) into the blood of a patient in the form of microbubbles or nanobubbles by dissolving the oxygen in a saline solution. How-ever, the amount of oxygen that a saline solution can dissolve at one atmospheric pressure may be small, resulting in the saline solution having low oxygen content. If such a saline solution were used for intravenous oxygen delivery, a substantial volume of saline solution may need to be delivered to satisfy the oxygen requirements of a patient, diluting the blood of the patient to an unsafe extent. Therefore, a one atmospheric pressure solution of dissolved oxygen is not a viable solution to deliver oxygen to patient tissues. Instead, as described further below, a system may provide a solution that is supersaturated with oxygen due to the oxygen being dissolved into the solution at a pressure greater than one atmosphere to increase the oxygen content per volume of fluid and deliver the supersaturated solution directly to the vasculature of a patient. By releasing the pressurized solution through a nozzle or other such structures, the dissolved oxygen may effervesce from the saline solution and form nanobubbles upon depressurization that remain suspended in blood and are absorbed by hemoglobin. Further, unlike larger bubbles, nanobubbles (or microbubbles in some examples) do not tend to obstruct blood from passing through microcirculatory vessels (e.g., vessels with diameters less than 1 mm), reducing the risk of embolism. Although the examples herein generally describe the generation or creation of nanobubbles less than 1000 nm in diameter, microbubbles greater than 1 micrometer and less than 100 micrometers, for example, may be created in some examples that may still provide gas delivery to tissues. Therefore, the devices and systems described herein may be configured to create microbubbles instead of, or in addition to, nanobubbles.

FIG. 1 is a conceptual diagram of an example system 100 configured to intravenously deliver a solution 102 including a pressurized fluid 104 ("fluid 104") supersaturated (i.e., saturated beyond a saturation point of fluid 104 at one atmospheric pressure (atm)) with a gas 106 to a target site 109 (which may be in a patient's body) via a flow channel 111 under controlled circumstances. Examples of target site 109 may include the vasculature of a patient, the gastrointestinal (GI) track for absorption of the gaseous solution with direct effect in the GI track and circulation, subcutaneously for absorption, intraosseously for immediate absorption in the venous system, etc. In some examples, fluid 104 may include saline. Gas 106 may include oxygen. As shown in FIG. 1, system 100 includes a fluid delivery device 108. In some examples, fluid delivery device 108 may include a capillary 110. Additionally or alternatively, fluid delivery device 108 may include a nozzle 112.

Capillary 110 may define a capillary inlet 114 and a capillary outlet 116. Capillary may define a capillary flow channel 118 (illustrated with a dashed outline) extending between capillary inlet 114 and capillary outlet 116. Flow channel 111 may include capillary flow channel 118. Capillary flow channel 118 may be configured to enable solution 102 to flow from capillary inlet 114 to capillary outlet 116 while maintaining a fluid pressure of solution 102. For example, the diameter of capillary flow channel 118 may be such that gas 106 dissolved within fluid 104 cannot (to some extent) depressurize and expand while solution 102 flows through capillary flow channel 118.

Capillary 110 may be configured to deliver solution 102 via capillary flow channel 118 such that gas 106 in solution 102 forms gas nanobubbles 136 (e.g., bubbles of gas 106 with a diameter less than about 1000 nm, or less than about 500 nm). For example, a diameter of a first portion 113A of capillary flow channel 118 may be greater than a diameter of a second portion 1113B of capillary flow channel 118, and the diameter of second portion 113B of capillary flow channel 118 may be less than a diameter of a third portion 113C of capillary flow channel 118, where first portion 113A is proximate to second portion 113B, and second portion 113B is proximate to third portion 113C. In this way, capillary flow channel 118 may constrict and expand, achieving the Venturi effect. Portions 113A-113C of capillary flow channel 118 may form a Venturi tube. In other words, in some examples, capillary 110 may include a venturi tube configured to form gas nanobubbles 136. In such examples, the Venturi tube may be proximate capillary outlet 116 such that gas nanobubbles 136 form outside of the patient's body (i.e., ex vivo) and before reaching target site 109.

The Venturi tube of capillary flow channel 118 may define a small opening that controls the flow rate of fluid 104. When fluid 104 supersaturated with gas 106 flows through the small opening, a microbubble mist may nucleate. Because the earlier stages of bubble growth involve "clustering" of gas 106 from solution 102 as the pressure decreases (e.g., in the portion of the Venturi tube where the diameter is constricting), a large number of nanometer-scale bubbles (e.g., gas nanobubbles 136) may form, as opposed to a single large bubble. Large bubble formation can be mitigated by decreasing the pressure from high pressure to atmospheric pressure quickly (in turn expanding the mixture), and by mixing the microbubble flow with venous blood prior to bubble-bubble collision and coalescence, leading to the formation of small-sized bubbles (e.g., bubbles with a diameter of about 5 to 100 nm).

In some examples, fluid delivery device 108 may include nozzle 112 (e.g., in addition or alternative to capillary 110). Nozzle 112 may define a nozzle inlet 120 and a nozzle outlet 122. Nozzle 112 may define a nozzle flow channel 124 extending between nozzle inlet 120 and nozzle outlet 122. Flow channel 111 may include nozzle flow channel 124. Nozzle flow channel 124 may be configured to establish fluid communication between capillary outlet 116 and nozzle inlet 120. As such, solution 102 may flow from capillary inlet 114 to nozzle outlet 122.

Nozzle 112 may be configured to deliver solution 102 via nozzle flow channel 124 such that gas 106 in solution 102 forms gas nanobubbles 136 (i.e., bubbles of gas 106 with a diameter less than approximately 500 nanometers). Gas nanobubbles 136 may form while solution 102 flow through nozzle flow channel 124 or after solution 102 is released at target site 109, such as within the vasculature of a patient, from nozzle outlet 122. For example, nozzle 112 be configured to form gas nanobubbles 136 by defining nozzle flow channel 124 such that a diameter of a first portion 115A of nozzle flow channel 124 is less than a diameter of a second portion 115B of nozzle flow channel 124, where first portion 115A is proximate to second portion 115B. In this way, a portion of nozzle flow channel 124 may be constricted, achieving the Venturi effect. In some examples, nozzle 112 may be a Venturi nozzle.

Thus, depending on the configuration of fluid delivery device 108, gas nanobubbles 136 may form while solution 102 flows through flow channel 111 or after solution 102 exits flow channel 111 within, for example, the body of a patient. For example, if fluid delivery device 108 includes capillary 110 configured to form gas nanobubbles 136 but not nozzle 112, gas nanobubbles 136 may form while flowing through capillary 110 and prior to exiting capillary 110, which may occur outside the patient's body. In another example, if fluid delivery device 108 includes nozzle 112 configured to form nanobubbles 136 but not capillary 110, gas nanobubbles 136 may form while flowing through or shortly after exiting nozzle 112. Nozzle 112 may be disposed within the patient's body such that gas nanobubbles 136 form in the patient's body.

To address the possibility of bubbles larger than gas nanobubbles 136 forming when solution 102 flows through flow channel 111, flow channel 111 may include a bubble trap configured to prevent the flow of larger bubbles. In other words, the bubble trap may be in line (e.g., distal to the Venturi tube of capillary 110) and deny entry of larger bubbles in the venous circulation. A bubble trap may be based on differential buoyancy of the larger bubbles. For example, larger bubbles may rise above a certain level in capillary 110 while smaller bubbles do not. In some examples, the bubble trap may define an exhaust vent at that certain level such that the larger bubbles flow through the exhaust vent while the smaller bubbles do not. Additionally or alternatively, the bubble trap may include a pump that applies a suction force at that certain level to separate the larger bubbles from gas nanobubbles 136 before intravenous infusion.

In any case, fluid delivery device 108 may release solution 102 at target site 109 at substantially 1 atm. For example, capillary 110 and/or nozzle 112 may release solution 102 within the vasculature of the patient at substantially 1 atm. In some examples, nanobubbles 112 may diffuse in the bloodstream of the patient in the form of a "mist" due to the number, density, size, and/or velocity of gas nanobubbles 136. When solution 102 is released at target site 109 (e.g., a patient's bloodstream), gas nanobubbles 136 within solution 102 may bind with hemoglobin 138, addressing the patient's metabolic requirements. For example, solution 102 may deliver oxygen nanobubbles that may readily release oxygen to bind with hemoglobin 138, addressing the patient's oxygen requirements (while bypassing the patient's lungs). Depending on the flow rate of solution 102, oxygen content of gas nanobubbles 136 may bind with all hemoglobin 138 (flowing in the vicinity of target site 109 at that time) such that all hemoglobin 138 is saturated. If an excess of gas nanobubbles 136 are delivered to target site 109, supersaturation may occur in which free gas nanobubbles 136 circulate around the patient's vasculature. The circulation of free gas nanobubbles 136 may result in direct oxygenation of tissue.

In some examples, system 100 include a container 140, a pressurization device 144, and a control circuitry 146. Fluid delivery device 108 may be configured to receive solution 102 from container 140 defining a cavity 142 (illustrated with a dashed outline configured to contain fluid 104 and gas 106. Pressurization device 144 (e.g., a piston, a pump, a compressor etc.) may be configured to pressurize fluid 104 and gas 106 within cavity 142 such that fluid 104 and gas 106 form solution 102. For example, pressurization device 11 may increase an amount (e.g., in mols) of gas 106 within container 140 while an amount of fluid 104 within container 140 remains the same. Control circuitry 146 may be configured to control pressurization device 144 to pressurize cavity 142. Control circuitry 146 may include processing circuitry (e.g., one or more processors or logic circuits) that controls one or more mechanical components configured to pressurize cavity 142, such as pressurization device 144.

Pressurizing fluid 104 and gas 106 within cavity 142 to form solution 102 may result in supersaturation of solution 102 with gas 106. For example, pressurization device 144 may pressurize saline and oxygen within cavity 142 to form a high oxygen content saline solution. The formation of solution 102 may be based on the principle that the solubility of gas 106 in fluid 104 may vary linearly with pressure such that an increase in the pressure within cavity 142 may increase the solubility of gas 106 in fluid 104. As such, increasing the pressure within cavity 142 from 1 atmospheres (atm) to 10 atm may increase the solubility of gas 106 in fluid 104, increasing the content of gas 106 within fluid 104. Similarly, increasing the pressure within cavity 142 from 10 atm to 100 atm may again increase the solubility of gas 106 in fluid 104, again increasing the content of gas 106 within fluid 104.

Fluid delivery device 108 may be configured to receive solution 102 from cavity of 142. For example, capillary inlet 114 may mechanically and fluidically engage with a container outlet 148 such that cavity 148 is in fluid communication with capillary 110. Pressurized solution 102 may flow through capillary flow channel 118. In some examples, container outlet 148 may include a valve 150 configured to control the flow rate of solution 102. In some examples, control circuitry 146 may be configured to control valve 150 to control the flow rate of solution 102.

In some examples, system 100 may include more than one capillary 110, in which case each of the capillaries may be similar, if not substantially similar, to capillary 110. In some examples, the flow rate of solution 102 may be proportional to the number of capillaries 110. By controlling the flow rate of solution 102 (e.g., by controlling valve 150 via control circuitry 146, increasing the number of capillaries 110, etc.), the rate of gas delivery may be controlled by adjusting the flow rate of solution 102.

In some examples, the efficacy of patient therapy that fluid delivery device 108 is configured to deliver may depend on a flow rate 152 of hemoglobin 138 ("hemoglobin flow rate 152") at target site 109. For example, venous, unsaturated hemoglobin 138 may act as an absorption sink. Hemoglobin flow rate 152 at a peripheral vein may be relatively low compared to hemoglobin flow rate 152 at a central vein. Accordingly, selecting a central vein as target site 109 may result in a greater rate of gas nanobubbles 136 binding to hemoglobin 138 (in this way, addressing the patient's metabolic requirements) than selecting a peripheral vein as target site 109.

Figure 2:
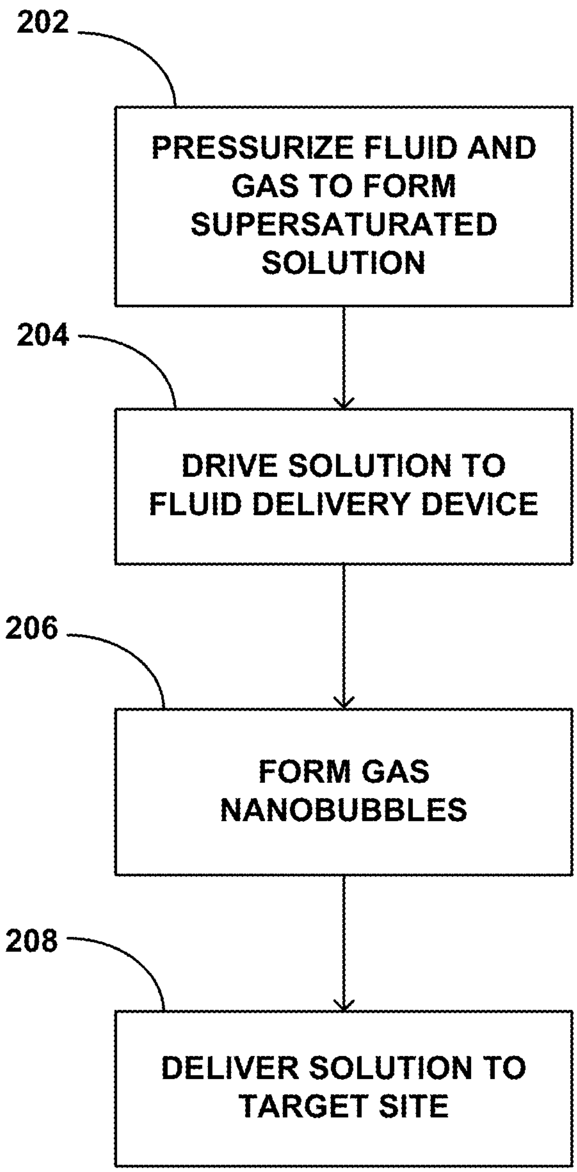
FIG. 2 is a flowchart of an example technique of using the system.

FIG. 2 is a flowchart of an example technique of using system 100 that includes both capillary 110 and nozzle 112. However, it should be understood that techniques described herein may be applied in a similar manner to a system that only includes capillary 110 (or a plurality thereof) or nozzle 112.

In some examples, pressurization device 144 may pressurize fluid 104 and gas 106 within cavity 142 such that fluid 104 and gas 106 form solution 102 (202).

Pressurizing fluid 104 and gas 106 within cavity 142 to form solution 102 may result in supersaturation of solution 102 with gas 106. For example, pressurization device 144 may pressurize saline and oxygen within cavity 142 to form a high oxygen content saline solution. In some examples, control circuitry 146 may be configured to control pressurization device 144 to pressurize cavity 142. Control circuitry 146 may include processing circuitry (e.g., one or more processors or logic circuits) that controls one or more mechanical components configured to pressurize cavity 142, such as pressurization device 144.

Fluid delivery device 108 may deliver solution 102 (204). For example, fluid delivery device 108 may receive solution 102 from cavity of 142 and deliver solution 102 via flow channel 111. In some examples, inlet 114 may mechanically and fluidically engage with a container outlet 148 such that cavity 148 is in fluid communication with capillary 110. Pressurized solution 102 may flow through capillary flow channel 118. Capillary flow channel 118 may be configured to enable solution 102 to flow from capillary inlet 114 to capillary outlet 116. In some examples, container outlet 148 may include a valve 150 configured to control the flow rate of solution 102. In some examples, control circuitry 146 may be configured to control valve 150 to control the flow rate of solution 102.

Nozzle 112 may deliver solution 102 via nozzle flow channel 124 such that gas 106 in fluid 104 forms gas nanobubbles 136 (206). For example, nozzle 112 may be configured to form gas nanobubbles 136 by defining nozzle flow channel 124 such that diameter of first portion 115A of nozzle flow channel 124 is less than a diameter of a second portion 115B of nozzle flow channel 124, where first portion 1I 5A is proximate to second portion 115B. In this way, a portion of nozzle flow channel 124 may be constricted, achieving the Venturi effect. In some examples, nozzle 112 may be a Venturi nozzle. In some examples, gas nanobubbles 136 may form when released directly into the blood. Additionally or alternatively, gas nanobubbles 136 may form while solution 102 flows through nozzle flow channel 124.

Fluid delivery device 108 may deliver solution 102 to target site at substantially 1 atm (208). In some examples, nozzle outlet 122 may release solution 102 such that gas nanobubbles 136 diffuse in the bloodstream of the patient in the form of a "mist" (due to the number, density, size, and/or velocity of gas nanobubbles 136). When solution 102 is released at target site 109 (e.g., a patient's bloodstream), gas nanobubbles 136 within solution 102 may bind with hemoglobin 138, addressing the patient's metabolic requirements. For example, solution 102 may deliver oxygen nanobubbles that may readily bind with hemoglobin 138, addressing the patient's oxygen requirements (while bypassing the patient's lungs). Depending on the flow rate of solution 102, gas nanobubbles 136 may bind with all hemoglobin 138 (flowing in the vicinity of target site 109 at that time) such that all hemoglobin 138 is saturated. If an excess of gas nanobubbles 136 are delivered to target site 109, supersaturation may occur in which free gas nanobubbles 136 circulate around the patient's vasculature. The circulation of free gas nanobubbles 136 may result in the oxygenation of tissue.

The techniques described herein may enable the delivery of large volumes of gas 106 in a safe volume of fluid 104 that satisfies the metabolic requirements of a patient. For example, the techniques may allow for the intravenous delivery of a large volume of oxygen in a supersaturated saline solution. By pressurizing the container 140 containing fluid 104 and gas 106, system 100 may transform fluid 104 into a supersaturated solution 102 infused with gas nanobubbles 136 that may be readily absorbed by hemoglobin 138. Capillary 110 of system 100 may then deliver fluid 104 along flow channel 118 under controlled circumstances and release solution 102 at target site 109 at substantially 1 atm. Due to the size of gas nanobubbles 136, the risk of an embolism may be greatly decreased. In this way, a large volume of gas 106 may be dissolved in a safe volume of fluid 104, and fluid 104 may be delivered in a manner that potentially avoids safety concerns, such as degassing, foaming, bubbling, and/or the like.

Figure 3A:
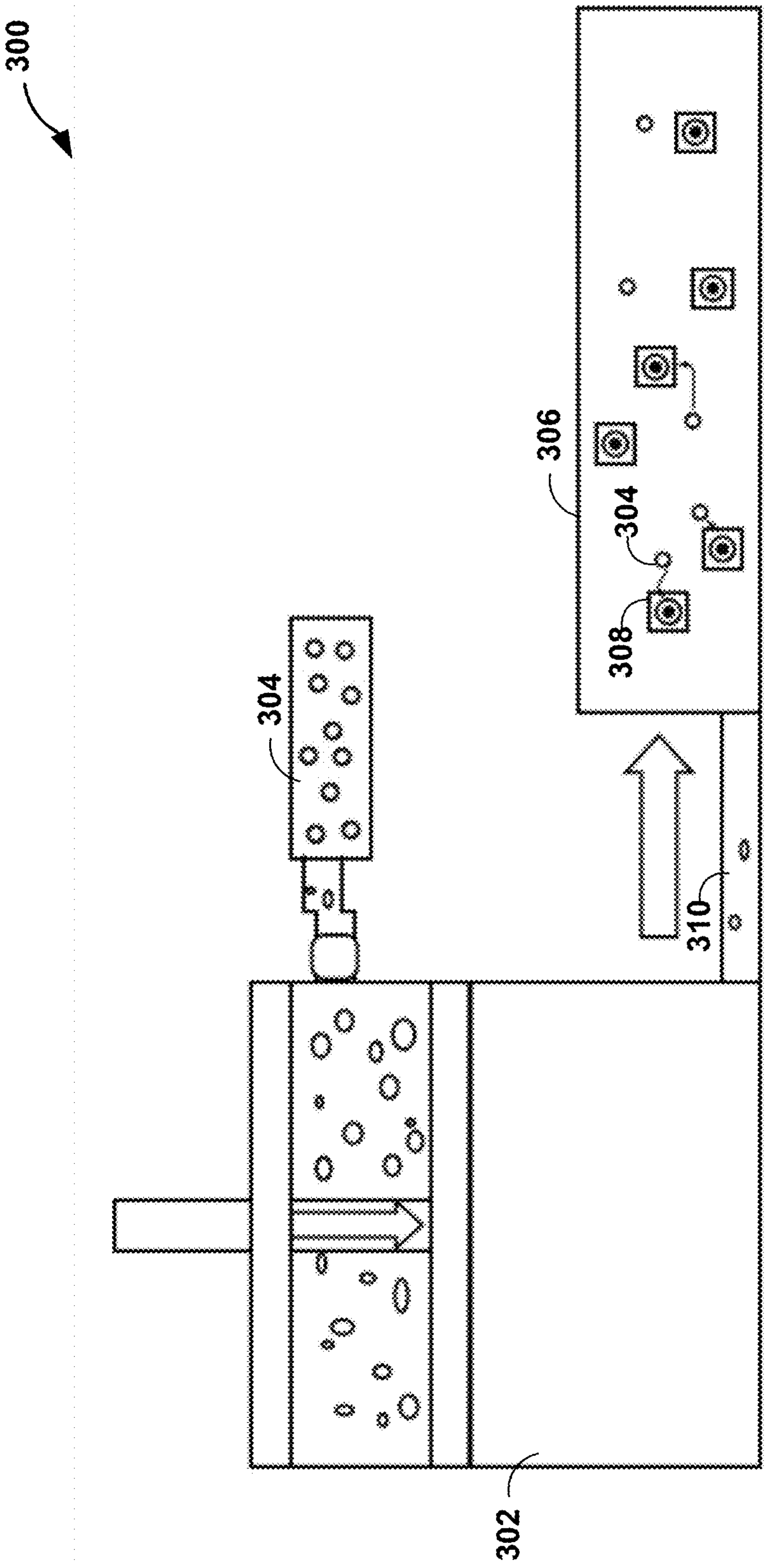
FIG. 3A is a conceptual diagram of an example system configured to intravenously deliver a saline solution infused with a large volume of oxygen, in accordance with one or more aspects of this disclosure.

FIG. 3A is a conceptual diagram of an example system 300 configured to intravenously deliver a saline solution 302 infused with a large volume of oxygen 304, in accordance with one or more aspects of this disclosure. As shown in FIG. 3, a mixture of degassed saline 302 and 100% oxygen 304 may be pressurized to allow for a large volume of oxygen 304 to be dissolved. Release of the pressure may be controlled by a nozzle/capillary/Pressure-flow regulator. Solution 302 may be released outside the body in a saline-filled regular IV tubing or directly in a vein 306 forming a "mist" consisting of saline and various nano/micro bubbles. Oxygen 304 may then be taken up directly by red cells 308 and the desaturated hemoglobin. Nanobubbles of the "target" size, e.g., less than about 1000 nm can easily go through capillaries, do not cause obstruction and could act as additional oxygen reservoir to directly replenish oxygen in tissues or red cells 308 as they continue circulating in vascular system.

When pressurized saline 302 with high oxygen content is released in an aqueous environment (e.g., target site 109) through a small opening (e.g., an outlet of capillary 110) that controls the flow rate, a microbubble or nanobubbles mist may nucleate. Because the earlier stages of bubble growth involve "clustering" of oxygen molecules 304 from a supersaturated solution 302 as the pressure decreases in a nozzle/capillary system 310, a large number of nanometer scale bubbles may form as opposed to a single large bubble. Large bubble formation can be mitigated by expanding the mixture from high pressure to atmospheric pressure quickly, and by mixing the microbubble flow with venous blood prior to bubble-bubble collision and coalescence leading to the formation of supermicrometer bubbles.

This observation may be consistent with nucleation studies of supersaturated vapor phase systems. Supersaturated vapor in a high-pressure system, when passing through nozzle/capillary system 310 to low pressure (and low temperature in this system), leads to the nucleation of nanoclusters and nanoparticles, as opposed to complete phase separation of the solid and surrounding vapor. Analogously, bubble nucleation in nozzle/capillary system 310 should, once properly designed, yield a relatively stable, well-dispersed bubbly flow, with sufficiently small bubbles to avoid ischemia and other complications. Therefore, by identifying a combination of pressure, temperature, ratio of dissolved oxygen/saline volume, and a type of outflow that controls the size distribution of the mist's bubble family (aim at a predominantly nm range), an infusate can be produced for intravenous injection.

Figure 3B:
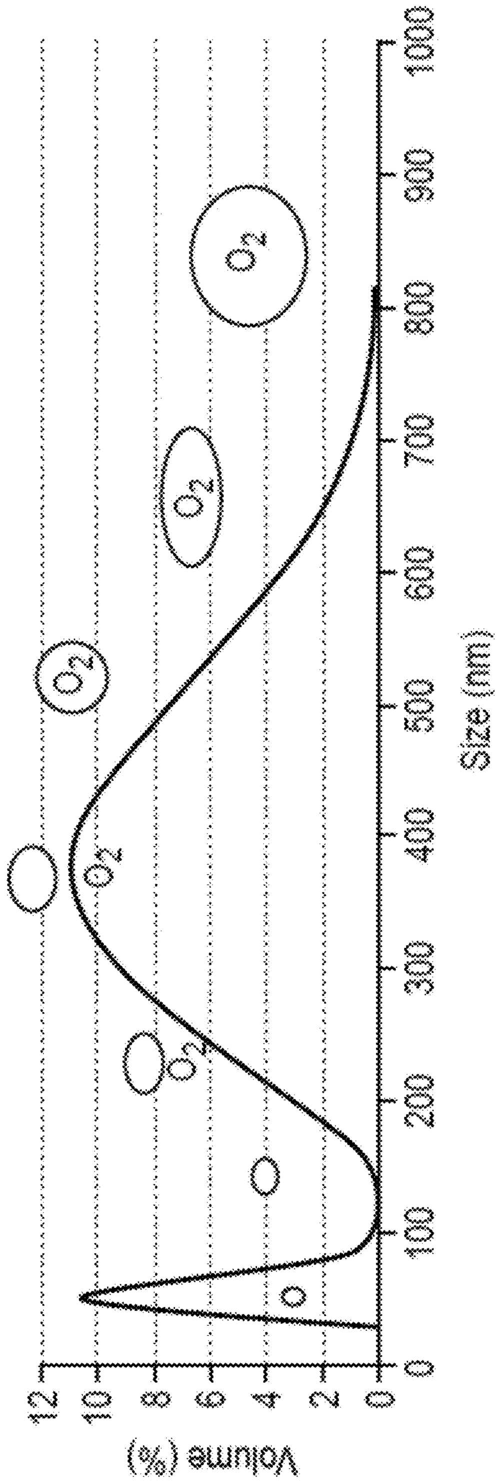
FIG. 3B is a chart illustrating distribution of bubble sizes.

FIG. 3B is a chart illustrating the distribution of oxygen bubbles having a particular bubble size in the infusate. As shown in FIG. 3B, about 10% of oxygen bubbles have a diameter of 100 nm or less. About 45% of oxygen bubbles have a diameter of 100 nm to 400 nm. About 45% of oxygen bubbles have a diameter of 400 nm to 800 nm.

One or more experiments conducted to evaluate the utility of the methods, systems, and devices of this disclosure are discussed in the following. In accordance with techniques of this disclosure, it was hypothesized that by using high pressure (e.g., 10-50 atm) and a saline temperature (4-25° C.) lower than the core body temperature of a patient, adequate volumes of oxygen could be dissolved in the infusate to make a clinically relevant therapy that can sustain body oxygen requirements for up to 5-20 minutes per liter of saline infused. The concept is based on the simple idea that when the highly pressurized solution is released under constant pressure (e.g., at 20 atm and 25° C.) through a nozzle (e.g. a Venturi tube) or capillary configured to control the size of oxygen bubble formation and flow rates, a "mist" consisting of oxygen nanobubbles and saline water molecules may be delivered for direct mixing with the returning venous blood. The ratio of the dissolved oxygen to saline may be about 1 L of $O_2$ to 1 L of saline.

Thus, the goal of the experiments was to evaluate the creation of a high-pressure, high-$O_2$ content, supersaturated saline solution that could act as the vehicle for the intravenous delivery of a "mist" of nanobubbles controlled by an appropriate "nozzle" configuration. It was hypothesized that the presence of venous, unsaturated hemoglobin would act as an absorption sink for the delivered $O_2$ mist. It was hypothesized that an optimal rate of mixing would be safe and minimize bubble formations through the process of immediate $O_2$ uptake.

Specific aims of the experiments were as follows. The first aim was to build a simple prototype compressor with an outflow system capable of connecting to different size and configurations of nozzles or capillaries to control the upper boundaries of the forming oxygen bubble size during depressurizing and flow generation. The second aim was to study the flow dynamics of the solution and mist characteristics under different upstream pressure/temperature conditions and during delivery of the solution at 1 atm. As used herein, mist refers to a mixture of bubbles and saline. Different pressure and temperature targets in combination with different size of nozzles and capillaries were used to control the flow rates and bubble nucleation process. The mist bubble size distributions were measured with laser diffraction and via various imaging techniques.

The third aim was to assess the effect of the optimal configuration, identified by achieving the second aim, for delivering the smaller size bubble distribution when it is infused at different rates into the venous system in a porcine model. A well-established VA-ECMO pig setup without an oxygenator was used, and the $O_2$ solution was infused directly into the ECMO tubing to study and optimize the rate of infusion. The effect of that infusion rate was evaluated.

The significance of the one or more experiments is discussed in the following. Mammalian blood is composed of cellular components, such as red and white blood cells, platelets, and plasma consisting of proteins, electrolytes, water, other molecules, and dissolved gasses. As blood passes through the lungs, oxygen from the lung alveolus (where the partial pressure of oxygen ($pO_2$) dissolved in the blood is approximately 100 millimeters of mercury (mmHg)) diffuses across the alveolar membrane to the venous blood ($pO_2$ typically about 40 mmHg at the pulmonary arterioles). As red cells transit through the exchange zone (e.g., where gas exchange occurs), oxygen diffusion equilibrates the partial pressure of the blood $PO_2$ maximally saturating hemoglobin such that the partial pressure of the arterial blood now has $PO_2$ of 100 mmHg as well. The greater the $pO_2$ gradient from the alveolar air to the blood plasma, the greater the oxygen diffusion rate and oxygen load of the circulating blood. Oxygen from the plasma rapidly equilibrates with the $pO_2$ inside red blood cells, where the oxygen is absorbed by the hemoglobin molecules in red blood cells. A means to continuously load the plasma with infused oxygen, which is then absorbed by hemoglobin, would facilitate transfer of oxygen to the blood and therefore to the body as the blood circulates.

Numerous medical emergencies stemming from inadequate oxygen delivery to tissues cost millions of lives and billions of dollars each year. A therapeutic intervention to support gas exchange and oxygen delivery to the blood has been positive pressure ventilation. Intravenous gas delivery has been considered lethal due to limitations related to bubble formation, slow absorption rates, and obstruction of microcirculation.

The problem with simple infusion of gaseous oxygen into the blood is that it forms large air bubbles and foam from the interaction of the surface tension of bubbles with blood proteins. As the air bubbles approach the microcirculatory vessels (e.g., vessels with diameters less than 1 mm), the surface tension of the bubbles prevents their passage though the circulation, creating an obstruction that stops blood flow. When introduced in sufficient quantity into the venous system, gas injection results in circulatory collapse due to obstruction of blood passing the lung. In the arterial system, gas injections of 1 ml or less can result in local tissue ischemia. This phenomenon is well-known, and extra precautions are regularly taken during medical procedures (e.g., a coronary angiography) to avoid exactly that. Additionally, the diffusion of gasses from the larger bubbles to the plasma is relatively slow. It is important though to state that most of the negative effects of gas bubbles derive from inert gas bubbles such as nitrogen since oxygen bubbles can be absorbed overtime. That is also evident by the contribution of nitrogen gas bubbles to the development of decompression diving sickness.

Microcirculation can pass particles less than about 15 micrometers (μm) in diameter (a typical red cell has a diameter of 7 to 10 μm), but air bubbles in the micrometer size typically coalesce in the blood and subsequently cause obstruction. Gas bubbles under 500 nm (for example), however, have significant surface energy and stay in solution until the gas diffuses into the surrounding solution.

The theoretical benefits of predominantly nm-size oxygen bubbles (e.g., nanobubbles) delivered intravenously are the following. Smaller diameter oxygen bubbles in solution offer a significantly larger surface area for gas exchange and uptake by circulating red blood vessel and hemoglobin. For the same volume of an oxygen bubble, the surface area available to interface with the blood increases proportionally to the reduction in its diameter (e.g., SA=6/D). For example, 1 mL of oxygen of 100 nm radius bubbles ($2\times10^{15}$ bubbles) has an exchange surface of 60 $m^2$ compared to 1 mL of 100 μm oxygen bubbles ($2\times10^6$ bubbles), which has an exchange surface of 0.06 $m^2$.

In addition, small oxygen bubbles (e.g., bubbles with a diameter less than about 1 μm) have smaller Weber numbers (e.g., a measure of the relative importance of the fluid's inertia compared to its surface tension) and are much less prone to coalesce and further remain well dispersed. Furthermore, small oxygen bubbles rise very slowly or not at all, as their terminal rising velocities are similar to or smaller than characteristic Brownian (diffusive) velocities.

A very important distinction between nanobubbles and larger bubbles is their ability to interact with the surrounding fluidic state and exchange oxygen molecules to achieve saturation equilibrium. The degree of saturation next to a bubble depends on the gas pressure within the bubble. Nanobubbles have higher internal pressure and release gas to dissolve under pressure into the surrounding undersaturated solution whereas larger bubbles grow by taking up gas from supersaturated solution; thus, small bubbles shrink and large bubbles grow (a process known as "Ostwald ripening"). For oxygen, which is a soluble gas, the pressure inside a bubble is inversely proportional to its diameter and for as low as 1 μm can be explained by the Laplace law of $P_{in}=P_{out}+3\gamma/D$, where $P_{in}$ and $P_{out}$ are the pressure inside and outside the bubble, D is the diameter and Y is the surface tension (N/m).

In theory, these are the characteristics that may be used in accordance with techniques of this disclosure. That is, venous blood with low partial pressure of oxygen can constantly absorb oxygen from the supersaturated proximity area surrounding the microbubble mist and progressively decrease the size of the oxygen nanobubbles until they are no longer present. If any nanobubbles manage to move to the arterial side without being absorbed, the nanobubbles can freely move through the capillaries and recirculate or allow for direct diffusion oxygenation at the tissue level when the oxygen pressure gradients favor exchange.

Generation of a high $O_2$ content supersaturated solution ($O_2$SSS) should allow direct infusion of a low normal saline volume/high $O_2$ content directly into the venous bloodstream, and the physical properties of the oxygen molecules either in direct solution or as nanobubbles can enable a means to replenish oxygen supplies during emergencies.

The innovation discovered from the one or more experiments is discussed in the following. The experiments indicated that very high pressures may be used to dissolve high volumes of oxygen in 1 L of saline. For example, at 20 atm and 25° C., the dissolved oxygen is 1:1 in volume with the saline (i.e., about 1 L of $O_2$ per 1 L of saline), allowing for 5 to 10 minutes of complete or almost complete coverage of the body oxygen requirements. At 40 atm, the same volume of $O_2$SSS can support the oxygen needs for about 15 to 20 minutes.

The ability of the $O_2$SSS to support the oxygen needs for such an extended period may be surprising, given that intuition might suggest that the dissolved oxygen would degas from solution all at once when delivered in the blood at one atmosphere of pressure. However, during the experiments, it was observed that when the pressurized saline with high oxygen content is released in an aqueous environment (which may be inside or outside a patient's body) through a small opening (e.g., a nozzle or capillary) that controls the flow rate, a microbubble mist nucleates. Because the earlier stages of bubble growth involve "clustering" of oxygen molecules from a supersaturated solution as the pressure decreases in the nozzle, a large number of nanometer scale bubbles first form, as opposed to a single large bubble. Large bubble formation can be mitigated by decreasing the pressure from high pressure to atmospheric pressure quickly (in turn expanding the mixture), and by mixing the microbubble flow with venous blood prior to bubble-bubble collision and coalescence, leading to the formation of small-sized bubbles (e.g., nanobubbles with a diameter of about 5 to 100 nm). In other examples, the nanobubbles may have a diameter less than about 500 nm or less than about 1000 nm.

This observation is consistent with nucleation studies of supersaturated vapor phase systems. Supersaturated vapor in a high-pressure system, when passing through a nozzle system to low pressure (and low temperature in this system), leads to the nucleation of nanoclusters and nanoparticles, as opposed to complete phase separation of the solid and surrounding vapor. Analogously, bubble nucleation in a nozzle system should, once properly designed, yield a relatively stable, well-dispersed bubbly flow, with sufficiently small bubbles to avoid ischemia and other complications. Therefore, by identifying a combination of pressure, temperature, ratio of dissolved oxygen/saline volume, and a type of outflow that controls the size distribution of the mist's bubble family (aim at a predominantly nm range), an infusate can be produced for intravenous injection.

The introduction of $O_2$SSS under high pressure directly in the venous blood stream may take advantage of the unique microbubble physical properties of high surface/internal pressure that would facilitate gas exchange with red cell hemoglobin and their ability to pass through the microcirculation without obstruction. Finally, it is possible that nanobubbles could allow for direct diffusion into tissues for any unbound-to-Hgb portion of oxygen content in solution at the arterial side.

The scientific background of the one or more experiments are discussed in the following. Known methods of generating a nanobubble saline solution at normal pressure were evaluated. Specifically, nanobubbles using normal saline, oxygen infusion, and high energy ultrasonication nanobubble oxygen solutions were generated in the laboratory. Gaseous oxygen was dissolved under pressure into physiologic saline with 0.9% NaCl by weight. The oxygen was infused through a simple bubbler that provides small bubbles in the 1 to 5 mm diameter range. The container of saline and the infused oxygen was then ensonified with 60 kHz frequency sound. The ultrasound resulted in no visible bubbles and supersaturation of the saline with oxygen. The solution was then vented by opening a pressure valve from the top and expelling the gas head, such that the remaining gas head was minimized, and pressure was maintained at 1 atm. The exact content in the solution was not measurable, but pig venous blood was used to measure the change of oxygen saturation of 100 ml of venous blood. Normal venous blood saturation initially had a Hgb of 14 gr/dl and was 68% saturated. The addition of another 50 cc 1:2 dilution of $O_2$ nanobubbles solution at 1 atm pressure and room temperature increased the saturation to 82%. Based on the difference in the oxygen bound to the hemoglobin, the content of oxygen present in the solution was 1.34 ml×14 gr of Hbx 0.14 (% Hgb saturation Δ)=2.6 ml $O_2$/50 ml of saline. That amounts to ~52 ml $O_2$/L of saline solution, or 25% of the basic metabolic needs per minute for a normal size adult (3 ml of oxygen/kg ~210-250 ml/min). Addition of regular saline alone had no effect on measured saturation.

The experiment was repeated 5 times and the average solution's concentration of dissolved oxygen was calculated to be 48.12 ml of $O_2$/L saline at 1 atm and room temperature. That is in general agreement with previously published evidence reporting a content of oxygen similar to the lower end of the experimental results, at 1 atm of 43 ml/liter of oxygen at room temperature. The presence of nanobubbles increases the dissolved oxygen content and provides approximately 30% more oxygen compared to nanobubbles with 100% oxygen. Finally, there were no detectable bubbles under the microscope of the mixed venous samples and $O_2$ solution.

Thus, normotensive $O_2$ saline solutions with or without nanobubbles cannot contain enough oxygen to offer any significant physiological and clinical effect in humans. Nonetheless, oxygen delivery intravenously in the form of nanobubbles seems to allow gas exchange and Hgb uptake of the oxygen available. If dissolved oxygen can be given intravenously for therapeutic reasons, high pressures may be used to raise the content to meaningful levels.

Figure 4A:
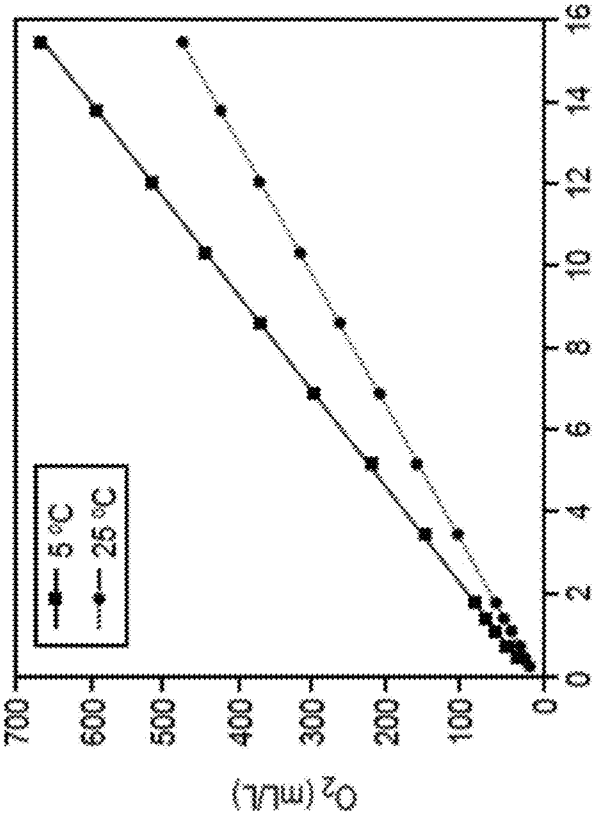
FIG. 4A is a chart illustrating example oxygen content in saline under different pressure conditions and different temperatures.

FIG. 4A is a chart illustrating oxygen content without nanobubbles ("NB") in ml/L in saline, shown under different pressure conditions and under 2 different temperatures. At 5° C. and 5 atm, 200 ml of oxygen per L of saline may be reached.

Figure 4B:
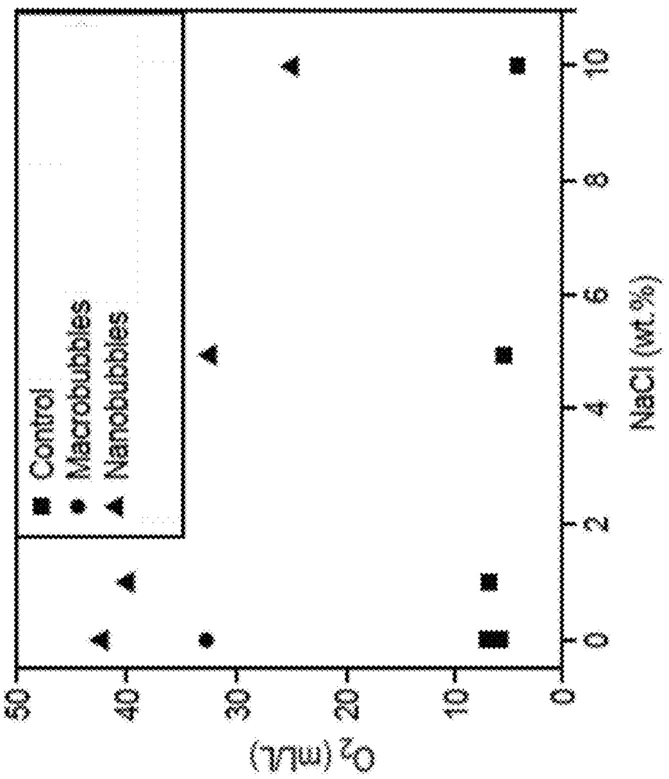
FIG. 4B is a chart illustrating example oxygen content in saline with and without nanobubbles.

FIG. 4B is a chart illustrating the effect of nanobubbles on oxygen content. Nanobubbles (triangles) are compared to control and macrobubbles (dots). The presence of NB appears to increase the content by ~30%, which may not be enough for a meaningful clinical application.

Figure 5A:
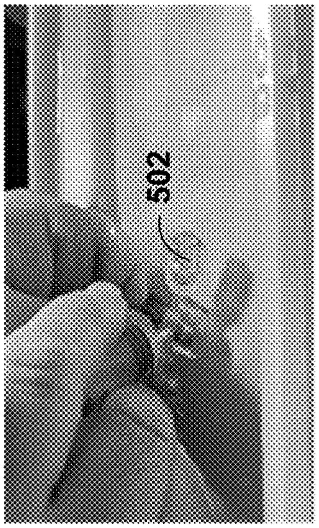
FIGS. 5A-C are photographs of an example system using a standard coronary balloon indeflator to deliver oxygen.
Figure 5B:
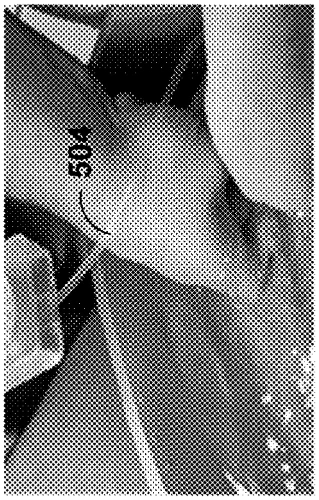
Figure 5C:
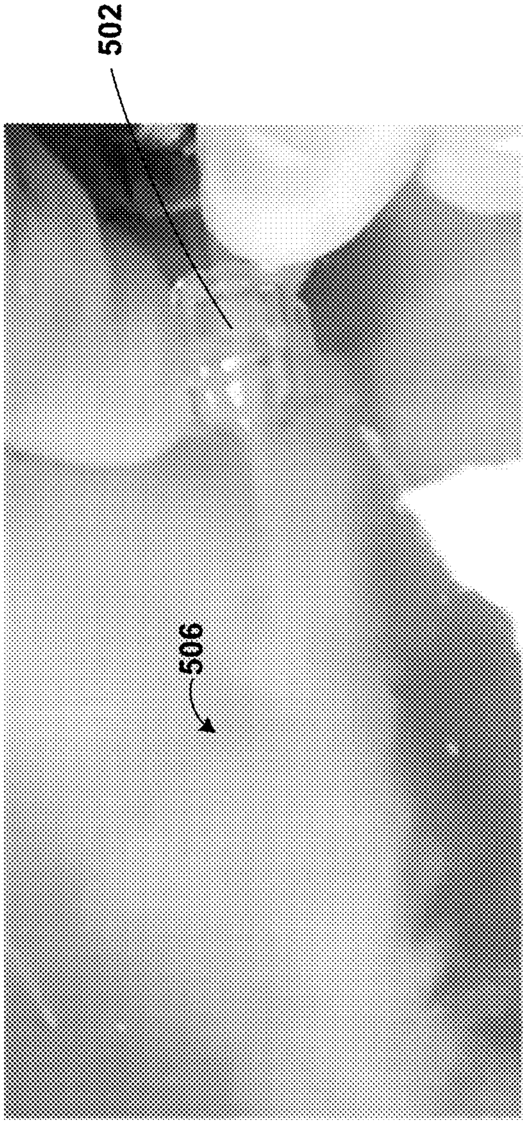

FIGS. 5A-C are photographs of a system using a standard coronary balloon to deliver oxygen. As discussed above, by using a standard coronary balloon indeflator, 12 ml of saline were mixed with 12 ml of 100% oxygen. Then the pressure was raised to 24 atm. At that pressure, there was no oxygen bubble present, proving that all the oxygen was dissolved. The end of a plastic tube 504 was connected to a high-pressure 3-way stopcock 502. The pressurized, 1:1, solution was then allowed to release by careful controlling of the 3-way stopcock opening of <1 mm in diameter under the surface of a saline bath open to air. Pressure in the chamber was maintained as high as possible during release by continuous clockwise rotation of the pressurizing plunger. Contrary to the initial expectations for generation of a single large or multiple smaller but coalescing bubbles, the formation of a mist 506 was observed. Mist 506 mainly stayed in solution with a visible shadow for a few seconds. Mist 506 was observed with variable success under repeated efforts.

The high-pressure stopcock 502 shown in FIG. 5A may be manually operated under the surface of a saline filled container to release the high $O_2$ content supersaturated solution ($O_2$SSS). As shown in FIG. 5B, high pressure (24 atm) saline/oxygen solution 1:1 in volume, may be released under the surface of saline bath using a high-pressure stopcock. The result was mist 506 of oxygen without large bubbles. As shown in FIG. 5C, the "milk" like appearance of the oxygen solution can be seen with a visible shadow at the bottom of the basin and an uninterrupted saline surface reflecting light, showing that there was no significant load of "macro" bubbles.

Figure 6A:
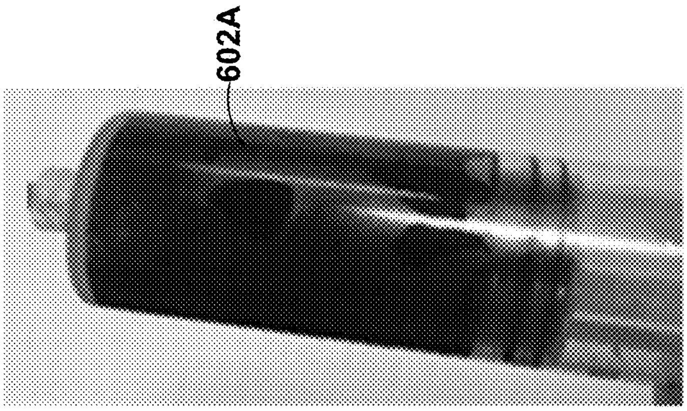
FIGS. 6A-6C are photographs of example venous blood from animal subjects indicating oxygen saturation thereof.
Figure 6B:
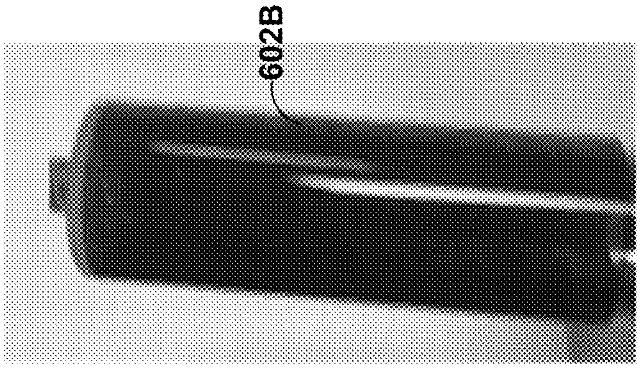
Figure 6C:
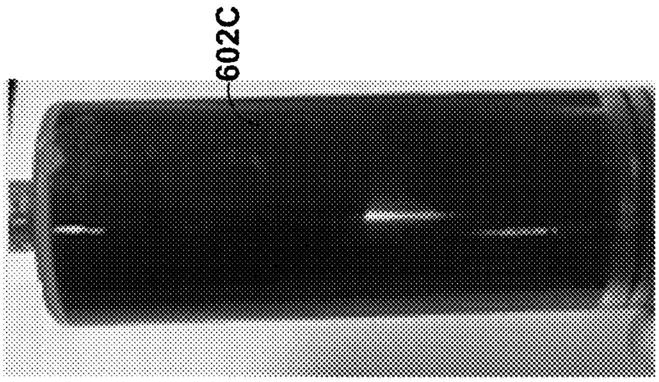

FIGS. 6A-6C are photographs of the venous blood from animal subjects indicating oxygen saturation thereof. Infusion of the indeflator's content in a 50 cc syringe with 30 cc mixed venous blood from the same animals showed a significant increase of oxygen saturation to 93% with a 1/3 dilution. A syringe 602A is filled with 30 cc of mixed venous blood and has an oxygen saturation of 68%. A syringe 602B is filled with 30 cc of mixed venous blood and 10 cc of $O_2$SSS and has an oxygen saturation of 93%. A syringe 602C is filled with 30 cc of mixed venous blood and 10 cc of NS and has an oxygen saturation of 68%. The color differences between the blood in syringe 602A and the blood in syringe 602B were not due to dilution effect as can be seen from the blood in syringe 602C. No image modification was applied.

The solution (described, for example, above with respect to FIGS. 6A-6C) delivered the mist though an arterial line kit in the femoral vein of 2 pigs. Transthoracic and transesophageal echocardiography detected only a handful of bubbles in the right ventricle. About 30 ml of $O_2$SSS was delivered with sequential release of the content of 3 indeflators (12 ml each) under 24 atm pressure (1 mL of saline was left behind to avoid delivering degassed oxygen bubbles located above the surface of the saline inside the indeflator as the pressure dropped during the infusion).

A continuous mixed venous $O_2$ Swan Ganz catheter was able to detect a 18-22% (from 68-72 to 89-93%) increase in the saturation for about 10 seconds. The release of the content of the indeflator in a single syringe with venous blood and the uptake of oxygen by the hemoglobin (Hgb) was immediate.

Figure 7:
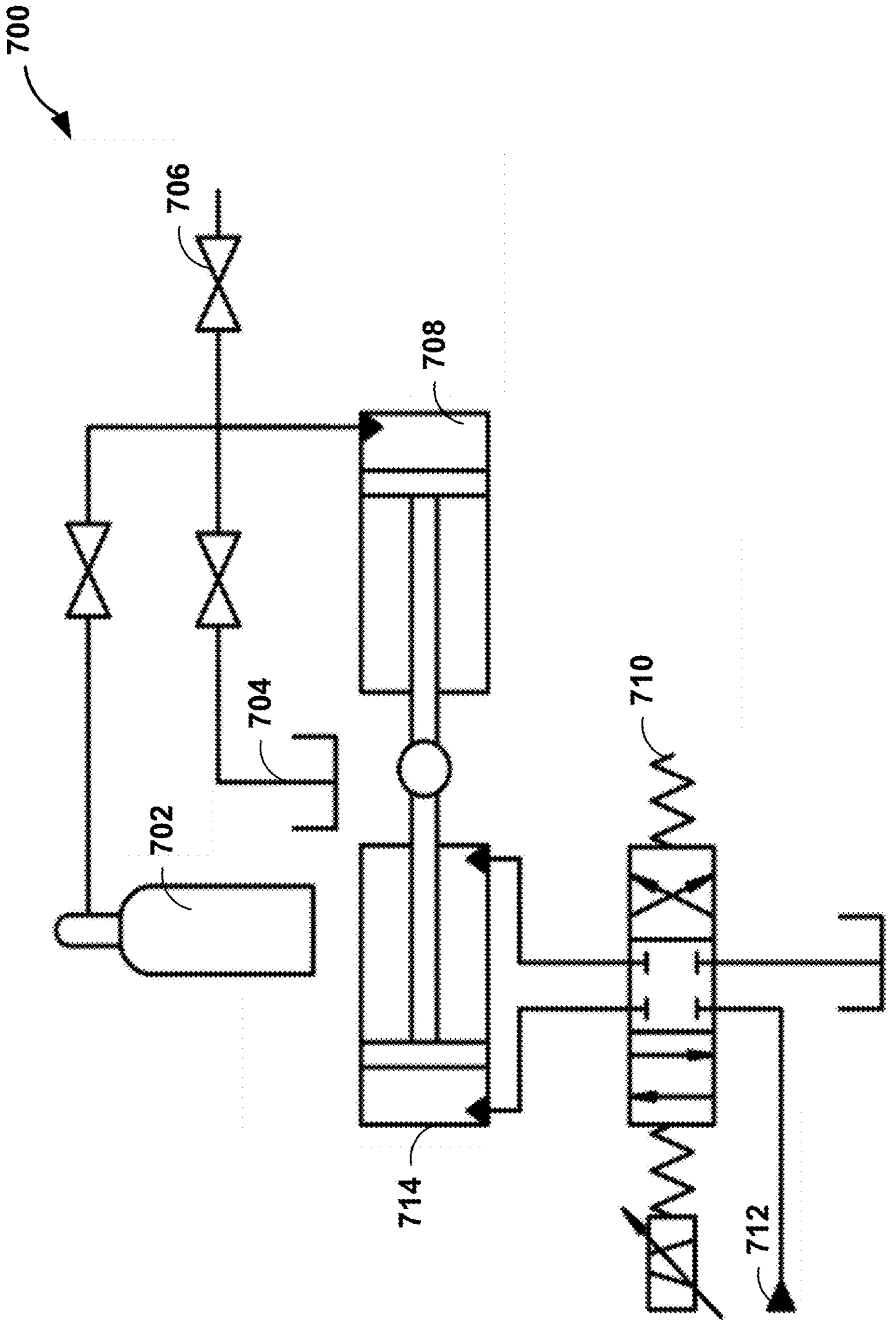
FIG. 7 is a schematic diagram of an example system configured to control the pressure inside a high-pressure chamber (10-100 atm) where large volumes of oxygen can be dissolved in degassed normal saline.

Proposed experimental designs for further evaluating the techniques are discussed in the following. FIG. 7 is a schematic diagram of a system 700 configured to control the pressure inside a high-pressure chamber (20-50 atm) where large volumes of oxygen can be dissolved in degassed normal saline. System 700 may include an oxygen source 702, a saline source 704, a bubble generator 706, a saline-oxygen compressor 708, a hydraulic cylinder 710, a servo valve 712, and a hydraulic power supply 714. System 700 may control the flow rate with a pressure regulator that maintains the chamber's pressure at the prespecified pressure to prevent degassing inside the chamber during release and flow generation while infusion. Bubble generator 706 may release a mixture of saline and large number of small diameter bubbles inside the blood. The release may be controlled by an arrangement of artificial capillaries or nozzles that control the flow rate and bubble formation and size in the venous aquatic environment.

Compressor 708 with 3-5 L capacity may be built that can allow for forward flow at constant flow rates (variable) while maintaining the pressure at a constant level to prevent degassing during the release phase. Compressor 708 may consist of 2 directly coupled linear hydraulic actuators. One actuator may be connected to hydraulic power supply 714 through servo valve 712. The second (stainless steel) actuator will intake the desired volume of saline and oxygen at atmospheric pressure. Using feedback control of servo valve 712 and feedback from a pressure transducer in the saline cylinder, the saline/oxygen solution may be compressed at the desired ramp rate to 20-40 atm. The pressure may be held constant as the oxygen dissolves, which may be observed by calculating the fluid volume in the saline cylinder from the measured piston rod position. The pressure may be maintained during the outflow of the saline/oxygen solution by maintain the feedback control of the servo valve.

The compressor conditions and outflow configurations that optimize the highest infusible oxygen flow rate with the smallest possible bubble size distribution may be identified and described. A set of experiments may be used in which different pressure/temperature conditions within clinical acceptable boundaries may be evaluated in a combination of different outlet configurations. The outflow configurations to be studied may include different nozzles with variable size openings and capillaries of various diameters and lengths, as well as numbers with the goal to control the flow rates to 0.5-2 ml/sec and deliver a range of oxygen rates from 100-300 ml/minute while delivering the minimum possible average oxygen bubble size with the target of less than about 500 nm in diameter. Straight, converging, or converging-diverging (e.g., de Laval/Venturi style) nozzle configurations, variable lengths (to control the rate of expansion), variable pressures (e.g., 10-50 atm), variable temperatures (e.g., 4-25° C.), and variable initial saturation of oxygen (e.g., 20%-100%) at pressure, etc., may be tested.

Laser diffraction (e.g., by using a Sympatec laser diffraction system) may be used to examine the bubble size distribution directly at the nozzle outlet (with the nozzle flow directly entering small tank with optical glass to facilitate measurements), and a unique digital inline holography may be used to directly image bubbles. Laser diffraction makes use of a monochromatic beam of light, which is scattered to variable angles by bubbles; the scattering signal as a function of angle is a direct function of the bubble size distribution interacting with the laser, and the Sympatec laser diffraction system utilizes built in data inversion routines to infer size distributions from scattered light signal.

Conversely, holography is a direct imaging technique wherein the diffraction from individual bubbles is observed and used to reconstruct bubble size and position. Laser diffraction and holography may be carried out at different locations along the nozzles examined, enabling the bubble size distribution evolution as a function of distance traversed in the nozzle to be examined. Combined, these instruments may enable the determination of bubble size distributions above 500 nm in size, and through conservation of mass (with knowledge of the starting dissolved oxygen content) the bubble fraction below 200 nm may be determined.

Nucleation of bubbles may also be monitored via temperature measurements (using a thermocouple inserted into the nozzle via a side port) because phase changes such as nucleation produce a temperature change (e.g., cooling in the case of bubble nucleation, akin to evaporative cooling). Through parametric studies of bubble size distributions, the identification of operating conditions yielding a high concentration of less than 500 nm diameter bubbles and a small concentration of greater than 500 nm diameter bubbles may be achieved.

Figure 8A:
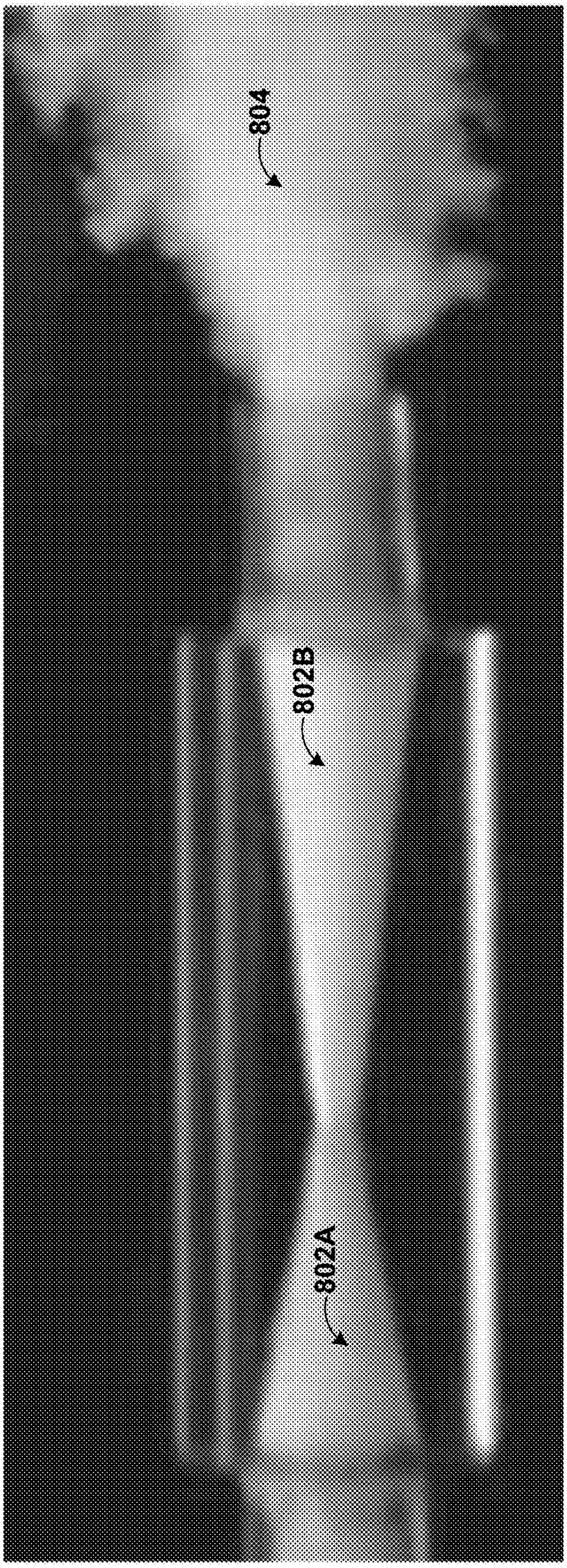
FIG. 8A is a photograph showing an example mechanism of nanobubble generation in a Venturi tube.

FIG. 8A is a photograph showing the mechanism of microbubble generation in a Venturi tube 800 (which may be referred to as a nozzle in some examples). Venturi tube 800 includes a portion 802A in which a diameter of Venturi tube 800 is gradually decreasing (e.g., converging) and a portion 802B in which a diameter of Venturi tube 800 is gradually increasing (e.g., diverging, expanding, etc.). As shown in FIG. 8A, Venturi tube 800 is outputting a mist 804 containing a large number of nanobubbles.

Figure 8B:
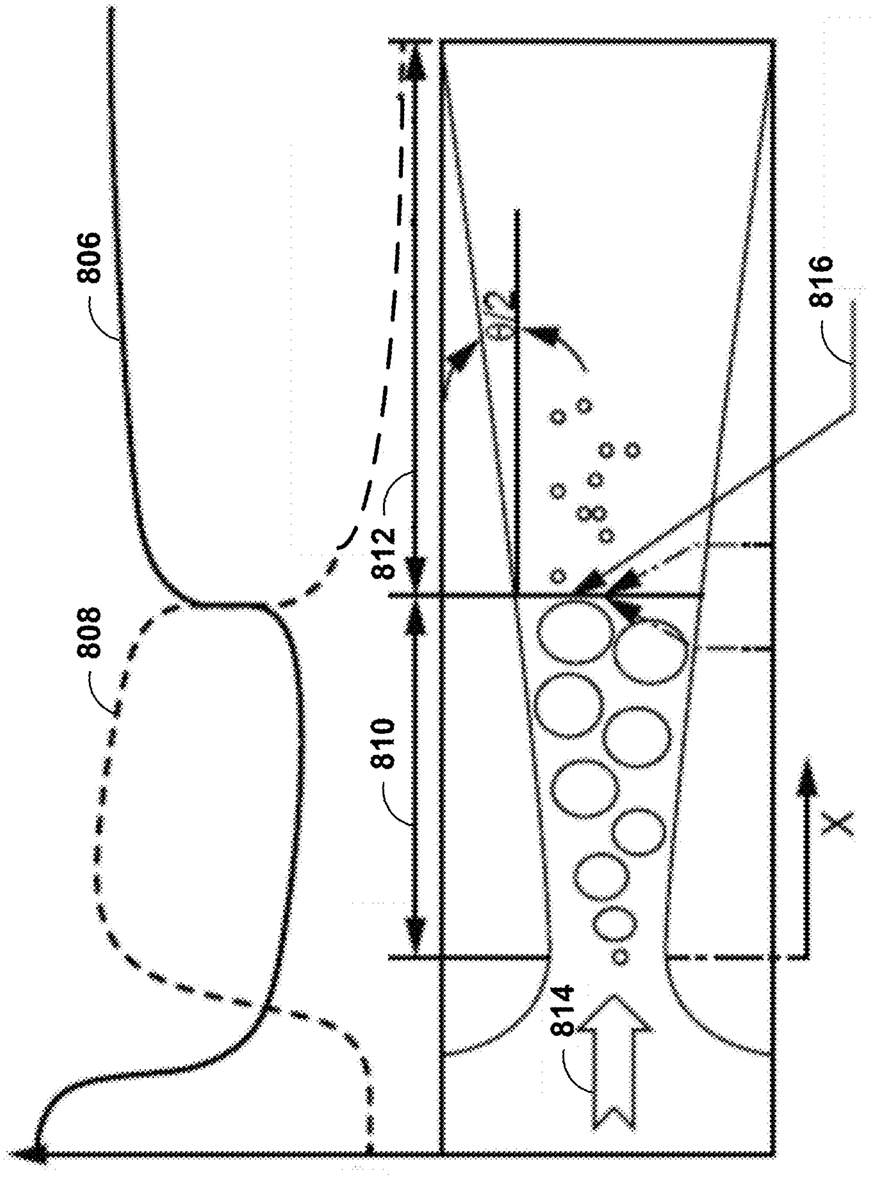
FIG. 8B is a diagram illustrating the mechanism of microbubble generation in the Venturi tube.

FIG. 8B is a diagram illustrating the physics of bubble cavitation and collapse due the shock wave dynamics. Solid line 806 represents pressure of the $O_2$SSS as it flows through a nozzle or capillary in accordance with techniques of this disclosure. Dashed line 808 represents velocity of the $O_2$SSS as it flows through the nozzle or capillary. Zone 810 represents a cavitating zone. Zone 812 represents a single-phase zone (e.g., an area in which cavities collapse). Arrow 814 represents the flow direction of $O_2$SSS. Vertical line 816 represents the shock position.

As illustrated in FIG. 8B, as $O_2$SSS flows through the nozzle or capillary, pressure 806 decreases and velocity 808 when the diameter of the nozzle or capillary converges (due to Bernoulli's principle). At the start of zone 810, bubbles of oxygen gas may begin to form (i.e., cavitate). As $O_2$SSS flows through zone 810, the bubbles may increase in size. However, once the $O_2$SSS reaches vertical line 816, the bubbles collapse and form nanobubbles. The bubbles remain as nanobubbles throughout zone 812. It should be understood that although described in this example as $O_2$SSS, the solution may comprise a fluid other than saline and a gas other than oxygen.

Methods for evaluation of the distribution of droplet size in aerosol formation have been described. Similar techniques may be modified for the purpose of identifying the size of the nanobubbles size characterization with the different configurations.

The process of forcing bubble cavitation and collapse due to acceleration and deceleration with pressure variation has been studied before for nonmedical applications, such as flotation devices in mineral processing using air and water. Forcing a highly pressure $O_2$SSS through a nozzle with the appropriate geometric configuration can consistently deliver a mist of oxygen that will facilitate absorption and not lead to larger bubble formation by coalescence.

Different nozzles sizes may be assessed for appropriate intravenous delivery rates. The diameters can vary based on the desired flow rates. Approximately 10 animals may be used to assess compatibility of the developed configurations with intravenous and intraosseous lines, as well as VA-ECMO tubing utilization and testing of macroscopic system failures while in operation and while infusing.

Figure 9A:
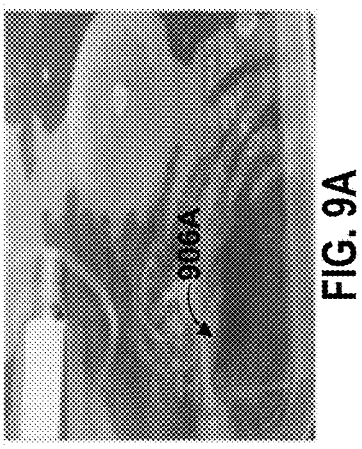
FIGS. 9A-9F are photographs showing example expansion of a saline solution infused with a large volume of oxygen.
Figure 9B:
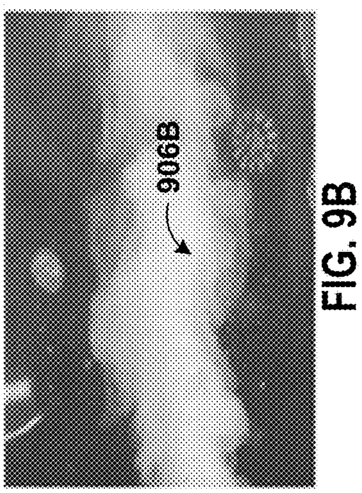
Figure 9C:
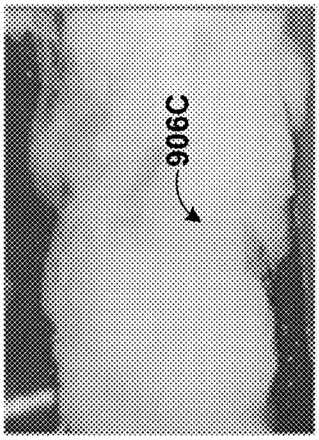
Figure 9D:
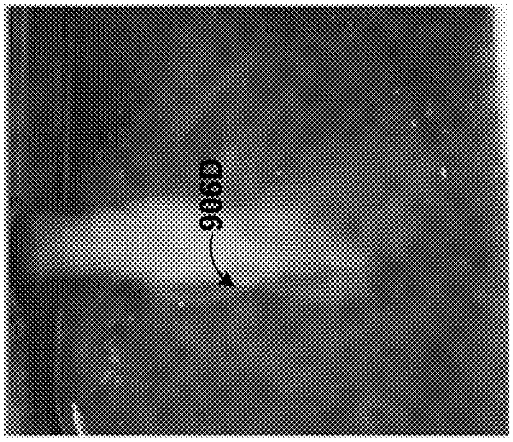
Figure 9E:
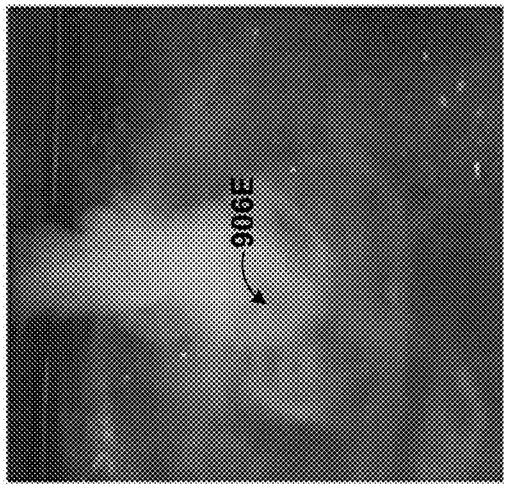
Figure 9F:
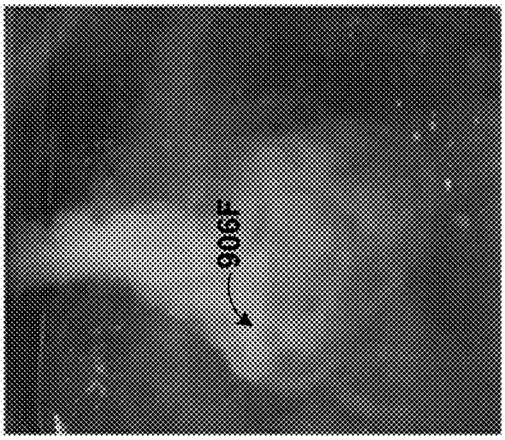

FIGS. 9A-9F are photographs showing expansion of $O_2$SSS 906A-906F (collectively, "$O_2$SSS 906") in a saline bath. In particular, FIGS. 9A-9C illustrate a high flow (e.g., 6 ml/s) of $O_2$SSS 906A-C in the saline bath, and FIGS. 9D-9F illustrate a low flow (e.g., 1 ml/s) of $O_2$SSS 906D-F in the saline bath. FIG. 9A shows the expansion of the high flow of $O_2$SSS 906A in the saline bath after 1 second. FIG. 9B shows the expansion of the high flow of $O_2$SSS 906B in the saline bath after 2 seconds. FIG. 9C shows the expansion of the high flow of $O_2$SSS 906C in the saline bath after 3 seconds. FIG. 9D shows the expansion of the low flow of $O_2$SSS 906D in the saline bath after 1 second. FIG. 9E shows the expansion of the low flow of $O_2$SSS 906E in the saline bath after 2 second. FIG. 9F shows the expansion of the low flow of $O_2$SSS 906F in the saline bath after 3 seconds.

A total of 100 ml of saline were mixed under 50 atm pressure and 25° C. with 250 ml of oxygen. The solution is then pushed under controlled pressure through a small needle to enter a saline filled tube, which is at 1 atm. $O_2$SSS 906 then enters in the 1 L saline container through a port and can be seen as a nebulous "jet". The "mist" stays in solution for a few minutes and the saline surface is intact without any bubbles forming. The appearance suggests the presence of nanobubbles and the absence of coalescing bubbles from the mist confirms their "molecule" like Brownian motion with degassing happening in a molecular level rather than bubble formation. The "mist" disappears after 3 to 4 minutes due to progressive degassing.

Thus, to reiterate, FIGS. 9A-9F show a supersaturated microbubble "mist" released at different rates under a saline surface. Large bubbles are absent, and the maintained integrity of the saline surface proves that there are no large bubble degassing effects. Instead, over time molecular "Brownian" degassing happens to bring the content of dissolved oxygen to the normal level under 1 atm.

Figure 10:
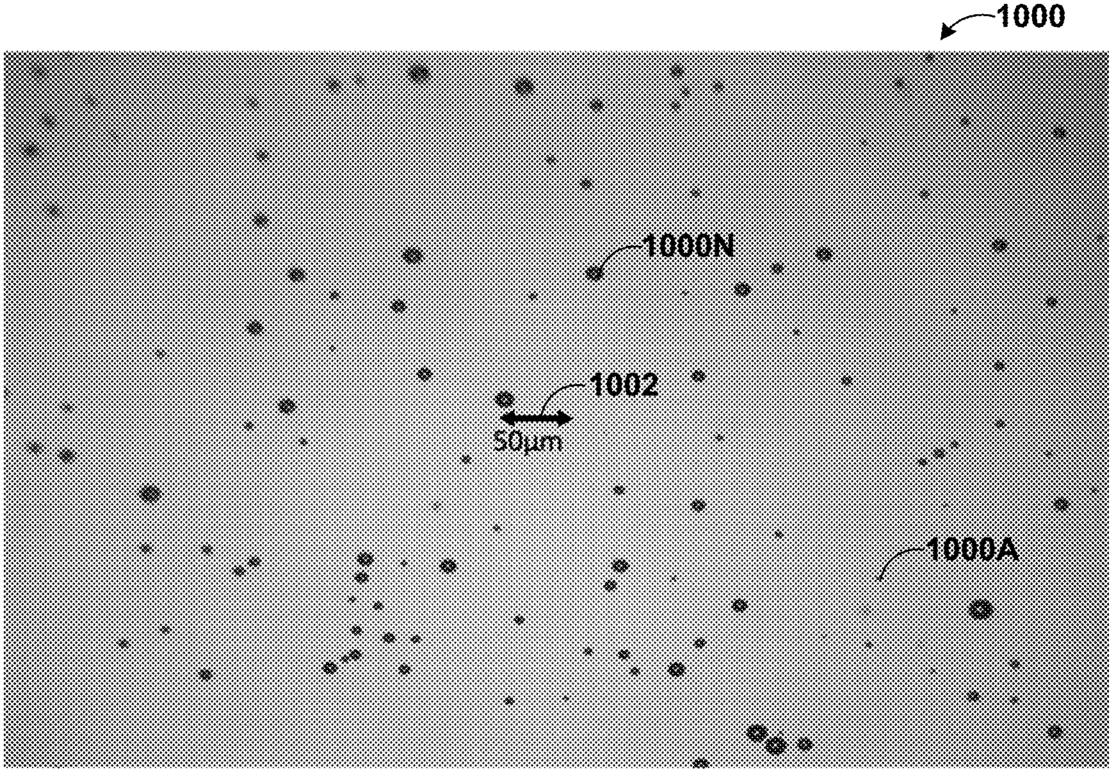
FIG. 10 is a photograph showing example oxygen nanobubbles generated in accordance with techniques of this disclosure.

FIG. 10 is a photograph showing the sizes of gas bubbles 1000A-1000N (collectively, "gas bubbles 1000"). FIG. 10 shows gas bubbles 1000 at low concentration under the microscope with a size calibration. Gas bubbles 1000 having diameters in the 1-10 μm range were generated with oxygen to saline mixture of ¼ and 50 atm of pressure released through a simple needle valve with 1/100 of an inch orifice diameter under 1 Atm normal atmospheric pressure and 25° C.

As indicated by a scale 1002 representing a length of 50 μm, each of gas bubbles 1000 has a diameter less than 50 μm. Several bubbles, such as gas bubble 1000A may be referred to as a nanobubble with a diameter less than 100 nm. However, other bubbles, such as gas bubble 1000N, has a diameter of about 500 nm or greater, which may be referred to as a nanobubble if less than 1000 nm. In any case, FIG. 10 shows that creating gas microbubbles and nanobubbles in accordance with techniques of this disclosure is feasible.

Figure 11A:
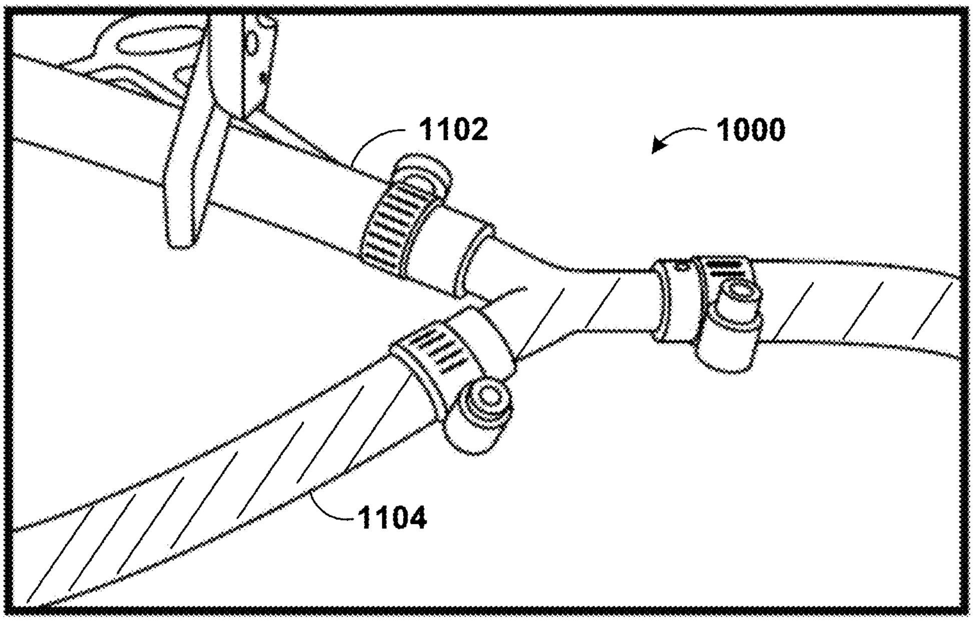
FIGS. 11A-11B are conceptual diagrams of an example ex-vivo, blood circulating configuration of a system in accordance with techniques of this disclosure.
Figure 11B:
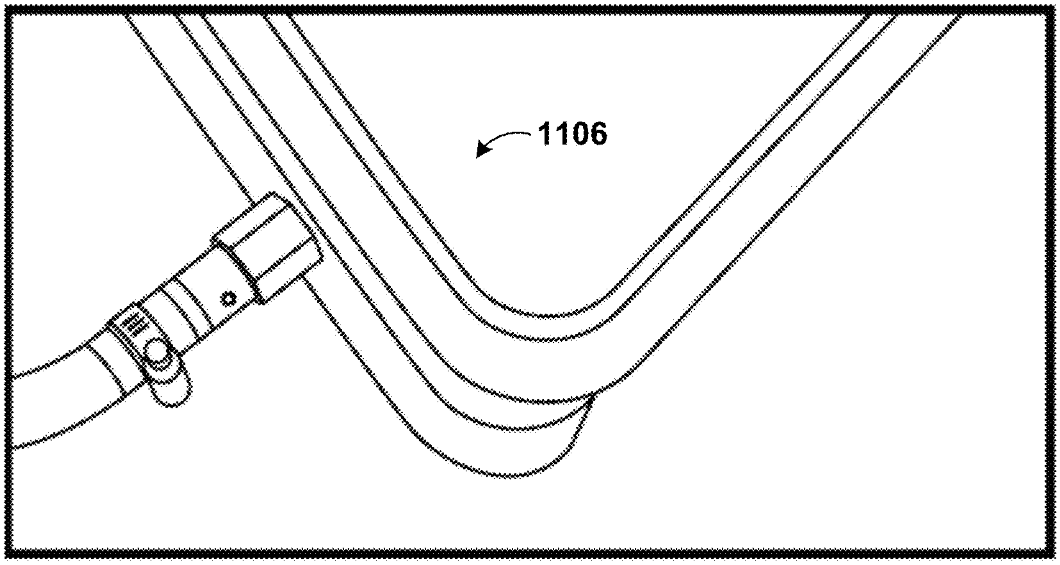

FIGS. 11A-11B are conceptual diagrams of an ex-vivo, blood circulating configuration of a system in accordance with techniques of this disclosure. The $O_2$SSS mist (illustrated as a white solution) enters, from a superior limb 1102 of a Y connector 1100, a blood stream (illustrated as a hatched solution) of the circuit flowing through an inferior limb 1104 of Y connector 1100. The direct introduction of a hypersaturated microbubble solution to a blood stream can be tested with different flow rates, blood saturation levels and different contents of oxygen. In conducted experiments, the introduction of the solution under 1 atm in circulating blood resulted in oversaturating the blood Hemoglobin and there were no immediate signs of larger babbles of foaming presence. The mixing was complete, and the oxygen "mist" was completely absorbed by incoming venous blood during the duration of its travel to a receiving container 1106 where it was fully saturated. In conducted experiments, the blood in receiving container 1106 was fully oxygenated and red.

Assessing the physiological effect of intravenous infusion of $O_2$SSS mist is discussed in the following. After identifying the highest concentration $O_2$SSS that can be delivered with the smallest average oxygen bubble size for flow rates that cover the minute oxygen consumption for at least 10-15 minutes/L of saline delivered, the following questions may need to be answered: 1. Can the $O_2$SSS infusate reliably and predictably increase venous blood saturation? 2. Is there a maximum rate of mixing with venous flow before obvious degassing occurs due to the inability of circulating Hgb to absorb the inflow of oxygen? Does venous $PO_2$ determines that rate? 3. What is the highest concentrated $O_2$SSS that can be delivered? 4. What happens with the released $CO_2$ and pH? 5. For how long can we support oxygenation with the infusion of the $O_2$SSS in the setting of hypoxic ventilation with 90/10% Heliox mixture? 6. What is the duration that a bolus infusion of 1-2 L $O_2$SSS can sustain oxygenation above 90% measured in the arterial side in a ventricular fibrillation model of cardiac arrest supported by VA-ECMO without the oxygenator?

To investigate these questions, an established porcine model of venoarterial circulatory support with standard VA-ECMO cannulas and the Cardiohelp circulatory support system without an oxygenator may be used. Each ECMO circuit can be used for multiple experiments with adequate cleaning and enzymatic wash out. In brief, a 25 French (Fr) ECMO venous cannula may be inserted though the right femoral vein under fluoroscopic guidance to the mid of the right atrium of 45-55 kg pigs. A 15 Fr arterial cannula may be inserted to the right femoral artery per standard techniques and both the cannulas may be connected with the circuit.

The circuit may be modified for purposes of the proposed experiments. The venous arm tubing may be very short and an additional 3 feet of tubing may be added after the pump head and oxygenator. Immediately after the pump a connector for the infusion of the $O_2$SSS may be added. That is important, because the ECMO "venous" side is a low-pressure system that is creating negative pressures for the intake of venous blood and may artificially promote degassing. The infusion of the $O_2$SSS after the pump ensures that it may be in a positive pressure environment similar to the venous system when low flow is present.

An additional oxygen saturation sensor may be placed after the $O_2$SSS infusion site down the circuit to assess Hgb levels and oxygenation as well as evaluate for detectable bubbles. The circuit may be clamped till the activation of the ECMO pump.

The animal experimental design is discussed in the following. All animals may be treated with 100 units per kg of heparin intravenous bolus, and activated clotting time may be kept above 200 seconds for the duration of the study. The Cardiohelp system controls the flow rate with a pump and can run flows from 0-5.0 L with the above-mentioned cannulas sizes. The system has built in venous and arterial side bubble detectors that may allow detection of macroscopic bubbles during the infusion of the $O_2$SSS. Continuous recording of Hgb and circuit pressures may be available to monitor the effects of the infused solution. The pig's tail may be connected to a side port of the arterial cannula to allow periodic sampling of arterial blood gasses (ABGs) for full blood gas and acid base balance characteristics. In this experimental setup, the pig may be consuming the infused oxygen, and a constant supply of venous desaturated blood may be available to investigate different rate infusions in the same animals.

The infusion of the $O_2$SSS may take place immediately after the ECMO pump/inert oxygenator with the insertion of a short 10 cm 7 Fr sheath oriented in the same direction of the cannula's flow. In that way, the fixed flow rate of $O_2$SSS may be traveling with the blood and may be mixing under different circuit flows ranging from 1-4 L/min in increments of 1 L/min held constant for a period of time (5-10 minutes). During that time extracorporeal venous and arterial side saturations may be recorded with progressively increasing flow rates of $O_2$SSS. Animal temperature may be kept with heat exchanged on the circuit at a stable 37° C. for the duration of the study per standard clinical standards. Animals may be kept sedated with inhaled anesthetics and may be breathing room air via a Drager ventilator (TV 8 cc/kg, on room air, PEEP 5 mmHg). The studies may be limited to a total of 3-4 liters of total saline volume infused in study increments over 2 hours.

Beating heart and ventilated models are discussed in the following. Once the relationship between the ratio of venous blood flow/infusion $O_2$SSS rate and oxygenation effect has been identified, the duration that one liter of $O_2$SSS can sustain oxygenation may be identified. Using the same experimental configuration, 95/5 Heliox mixture may be used to ventilate the animal for 5 minutes or until arterial saturation is recorded to be less than 85%. At that point, an infusion of $O_2$SSS may start below the optimal rate identified above and may be increased progressively to reach either normal arterial saturation, greater than 92% arterial saturation, or the highest possible at the highest rate (e.g., for a 2:1 Oxygen/saline solution (e.g., 200 ml of oxygen mist may be delivered with every 100 ml of saline, giving us an initial infusion rate of 1 ml/second and progressively increasing it to up to 5 ml/seconds). The infusion rate reaching a saturation of >90% at the arterial side (car or lip probe) may be sustained for up to 30 minutes or until 2 L of infusate have been delivered (which comes first).

Continuous extracorporeal blood gasses may be taken and ABGs venous and arterial may be obtained every 5 minutes. Samples of blood from the arterial cannula may be viewed under microscope to look for evidence of foam or macroscopic bubbles. If the oxygenation of the animal cannot be raised with the infusion at some point because of Hgb dilution, the animals can be rescued with initiation of the ECMO's oxygenator.

Ventricular Fibrillation, non-breathing, VA-ECMO supported models are discussed in the following. The animals may be anesthetized with Propofol. They may be paralyzed and the heart may be fibrillated per standard methodology. The animals then may be started on the VA-ECMO circuit with a flow of 3-3.5 L/min with room air. Subsequently, the ECMO flow may be decreased to 0.5-1.0 L/minute to simulate the blood flow that would be generated with cardiopulmonary resuscitation (CPR). Under these conditions, the saturation of the arterial side may decrease below 85% after a few minutes and the sweep speed can be adjusted (usually between 1-4 L/min of room air) to sustain it at that level.

The infusion of $O_2$SSS mist may be delivered at the highest rate possible (anticipated to be 3-5 ml/second) through either the intraosseous or the central line (e.g., for 10 animals). After 5 minutes of infusion and documentation of the blood gasses venous and arterial, the flow of air may be terminated in the oxygenator simulating failed airway and blood gasses may be collected every 5 minutes or till the saturation drops below 80%. That may assess the role of the nanobubbles to act as an additional reservoir for oxygenation. Once this is reached, the oxygenator and flow rates may increase to support the animal again at full flow and oxygen and allow for stabilization but maintaining the heart in ventricular fibrillation. After 10 minutes of stabilization and blood gas normalization the same process may be repeated with the infusion of the bolus may go through the other line compared to the initial infusion site (IO vs IV). Efficiency of the 2 sites may be assessed and compared. Animals may be evaluated with continuous central arterial pressure, intracranial pressure, carotid blood flow and intracardiac echocardiography.

A prolonged CPR study is discussed in the following. An animal study of prolonged CPR may be performed. In general, a very large number of CPR pig studies have been performed to assess physiological endpoints. A standard methodology may be followed. For example, electrically induced ventricular fibrillation (VF) may stay untreated for 3 minutes followed by 10 minutes of basic life support (BLS) and 10 minutes of Advanced Cardiovascular Life Support (ACLS). Standard aortic pressure, right atrial pressure, intracranial pressure, carotid flow, $ETCO_2$ may be recorded continuously. CPR may be performed with an automated CPR device for pigs also per standard protocol. To negate the confounding effects of ventilation and study the ability of the $O_2$SSS mist to adequately deliver oxygen for a short but critical period, both groups may receive no ventilation assistance throughout the study. Instead, the airway may be left open with the ET tube and chest compression only CPR may be performed. Using this protocol, it can be determined whether the control animals have adequate $PaO_2$ (e.g., about 40 mmHg) after 7-10 minutes of resuscitation as previously shown in published work.

The animals may be randomized to: 1) an infusion of 60 ml/min of $O_2$SSS mist starting at minute 5 of CPR (EMS arrival) group; or 2) a control group. Infusion of the $O_2$SSS may happen either through the IO or the IV route and may deliver about 1000 ml of saline and about 2 to 3 L of oxygen over the 15 minutes of CPR. At minute 20 of CPR, defibrillation may be attempted every 3 to 5 minutes for up to another 15 minutes of resuscitation efforts. If return of spontaneous circulation (ROSC) is not achieved the study may be terminated and the animals may be declared dead.

With 20 animals, the study may evaluate (with 80% power) the hypothesis that 80% ($O_2$SSS group) versus 20% (controls) of animals randomized to each group may have an arterial saturation of >90% (PaO2>60 mmHg) after 20 minutes of CPR. ABGs and arterial lactic acid every 5 minutes may be evaluated.

Animals that achieve ROSC may be followed for another 2 hours. Measures may include serial echocardiographic evaluation (q30 min) of the left ventricular function, troponin, and S100 B from venous blood at 2 hours, and terminal histological assessment of the heart with 2,3,5-triphenyltetrazolium (TTC) to detect possible microinfarctions.

This disclosure includes various examples, such as the following examples.

Example 1: A system includes a fluid delivery device configured to deliver gas nanobubbles to a target site of a patient from a solution including a fluid supersaturated with a gas, wherein the fluid delivery device defines a flow channel configured to flow the solution through the flow channel such that the gas in the supersaturated fluid forms gas nanobubbles as the solution flows through the flow channel towards the target site, and wherein the gas nanobubbles remain in the fluid at least until delivery to the target site.

Example 2: The system of example 1, wherein the fluid delivery device includes a capillary defining a capillary flow channel extending from a capillary inlet to a capillary outlet defined by the capillary, and wherein the flow channel includes the capillary flow channel.

Example 3: The system of example 2, wherein the capillary is configured to cause the formation of gas nanobubbles from the supersaturated fluid by defining the capillary flow channel to include: a diameter of a first portion of the capillary flow channel is greater than a diameter of a second portion of the capillary flow channel, wherein the diameter of the second portion of the capillary flow channel is less than a diameter of a third portion of the capillary flow channel, and wherein the first portion is proximate to the second portion and the second portion is proximate to the third portion.

Example 4: The system of example 2 or 3, wherein at least a portion of the capillary defines a Venturi tube.

Example 5: The system of any of examples 1 through 4, wherein the fluid delivery device includes a nozzle defining a nozzle flow channel extending from a nozzle inlet and a nozzle outlet defined by the nozzle, and wherein the flow channel includes the nozzle flow channel.

Example 6: The system of example 5, wherein the nozzle is configured to facilitate the formation of gas nanobubbles by defining the nozzle flow channel such that a diameter of a first portion of the nozzle flow channel is less than a diameter of a second portion of the nozzle flow channel.

Example 7: The system of example 5 or 6, wherein the nozzle is a Venturi nozzle.

Example 8: The system of any of examples 1 through 7, further includes a container defining a cavity configured to contain the fluid and the gas; and a pressurization device configured to pressurize the fluid and the gas within the cavity such that the fluid and the gas form the solution.

Example 9: The system of any of examples 1 through 8, wherein the fluid includes saline and the gas includes oxygen.

Example 10: The system of any of examples 1 through 9, further including a bubble trap configured to prevent gas nanobubbles having a diameter greater than or equal to a threshold size from flowing toward the target site, wherein the bubble trap is in fluid communication with the flow channel.

Example 11: The system of any of examples 1 through 10, wherein the target site is at least one of a vasculature of the patient, a gastrointestinal tract of the patient, a tissue of a patient, or a bone of a patient.

Example 12: A method includes delivering, via a fluid delivery device, gas nanobubbles to a target site of a patient from a solution including a fluid supersaturated with a gas, wherein the fluid delivery device defines a flow channel configured to flow the solution through the flow channel such that the gas in the supersaturated fluid forms gas nanobubbles as the solution flows through the flow channel towards the target site, and wherein the gas nanobubbles remain in the fluid at least until delivery to the target site.

Example 13: The method of example 12, wherein the fluid delivery device includes a capillary defining a capillary flow channel extending from a capillary inlet to a capillary outlet defined by the capillary, and wherein at least a portion of the capillary flow channel defines a Venturi tube.

Example 14: The method of example 12 or 13, wherein the fluid delivery device includes a nozzle defining a nozzle flow channel extending between a nozzle inlet and a nozzle outlet defined by the nozzle, and wherein the nozzle is a Venturi nozzle.

Example 15: The method of any of examples 12 through 14, wherein the fluid includes saline and the gas includes oxygen.

Example 16: The method of any of examples 12 through 15, wherein delivering the gas nanobubbles includes forming the gas nanobubbles in-vivo.

Example 17: The method of any of examples 12 through 16, wherein delivering the gas nanobubbles includes forming the gas nanobubbles ex-vivo.

Example 18: The method of any of examples 12 through 17, wherein the target site is at least one of a vasculature of the patient, a gastrointestinal tract of the patient, a tissue of a patient, or a bone of a patient.

Example 19: The method of any of examples 12 through 18, wherein delivering the solution includes delivering the solution to the target site that is subcutaneous.

Example 20: The method of any of examples 12 through 19, wherein delivering the solution includes delivering the solution intraosseously.

One or more of the techniques described in this disclosure may be implemented, at least in part, in hardware, software, firmware or any combination thereof. For example, various aspects of the described techniques may be implemented within one or more processors or processing circuitry, including one or more microprocessors, digital signal processors (DSPs), application specific integrated circuits (ASICs), field programmable gate arrays (FPGAs), graphics processing units (GPUs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

Various examples have been described. These and other examples are within the scope of the following claims.

What is claimed is:

1. A system comprising:

a fluid delivery device configured to deliver gas nanobubbles to a target site of a patient from a solution comprising a fluid supersaturated with a gas, wherein the fluid delivery device defines a flow channel configured to flow the solution through the flow channel such that the gas in the supersaturated fluid forms the gas nanobubbles having a diameter less than 500 nanometers (nm) as the solution flows through the flow channel towards the target site, and wherein the gas nanobubbles remain in the fluid at least until delivery to the target site.

2. The system of claim 1, wherein the fluid delivery device comprises a capillary defining a capillary flow channel extending from a capillary inlet to a capillary outlet defined by the capillary, and wherein the flow channel comprises the capillary flow channel.

3. The system of claim 2, wherein the capillary is configured to cause the formation of gas nanobubbles from the supersaturated fluid by defining the capillary flow channel to comprise:

a diameter of a first portion of the capillary flow channel is greater than a diameter of a second portion of the capillary flow channel, wherein the diameter of the second portion of the capillary flow channel is less than a diameter of a third portion of the capillary flow channel, and wherein the first portion is proximate to the second portion and the second portion is proximate to the third portion.

4. The system of claim 2, wherein at least a portion of the capillary defines a Venturi tube.

5. The system of claim 1, wherein the fluid delivery device comprises a nozzle defining a nozzle flow channel extending from a nozzle inlet and a nozzle outlet defined by the nozzle, and wherein the flow channel comprises the nozzle flow channel.

6. The system of claim 5, wherein the nozzle is configured to facilitate the formation of gas nanobubbles by defining the nozzle flow channel such that a diameter of a first portion of the nozzle flow channel is less than a diameter of a second portion of the nozzle flow channel.

7. The system of claim 5, wherein the nozzle is a Venturi nozzle.

8. The system of claim 1, further comprising:

a container defining a cavity configured to contain the fluid and the gas; and a pressurization device configured to pressurize the fluid and the gas within the cavity such that the fluid and the gas form the solution.

9. The system of claim 1, wherein the fluid comprises saline and the gas comprises oxygen.

10. The system of claim 1, further comprising a bubble trap configured to prevent gas nanobubbles having a diameter greater than or equal to a threshold size from flowing toward the target site, wherein the bubble trap is in fluid communication with the flow channel.

11. The system of claim 1, wherein the target site is at least one of a vasculature of the patient, a gastrointestinal tract of the patient, a tissue of a patient, or a bone of a patient.

12. The system of claim 1, wherein the diameter of the gas nanobubbles is from 5 nm to 100 nm.

13. A method comprising:

delivering, via a fluid delivery device, gas nanobubbles to a target site of a patient from a solution comprising a fluid supersaturated with a gas, wherein the fluid delivery device defines a flow channel configured to flow the solution through the flow channel such that the gas in the supersaturated fluid forms the gas nanobubbles having a diameter less than 500 nanometers (nm) as the solution flows through the flow channel towards the target site, and wherein the gas nanobubbles remain in the fluid at least until delivery to the target site.

14. The method of claim 13, wherein the fluid delivery device comprises a capillary defining a capillary flow channel extending from a capillary inlet to a capillary outlet defined by the capillary, and wherein at least a portion of the capillary flow channel defines a Venturi tube.

15. The method of claim 13, wherein the fluid delivery device comprises a nozzle defining a nozzle flow channel extending between a nozzle inlet and a nozzle outlet defined by the nozzle, and wherein the nozzle is a Venturi nozzle.

16. The method of claim 13, wherein the fluid comprises saline and the gas comprises oxygen.

17. The method of claim 13, wherein delivering the gas nanobubbles comprises forming the gas nanobubbles in-vivo.

18. The method of claim 13, wherein delivering the gas nanobubbles comprises forming the gas nanobubbles ex-vivo.

19. The method of claim 13, wherein the target site is at least one of a vasculature of the patient, a gastrointestinal tract of the patient, a tissue of a patient, or a bone of a patient.

20. The method of claim 13, wherein delivering the solution comprises delivering the solution to the target site that is subcutaneous.

21. The method of claim 13, wherein delivering the solution comprises delivering the solution intraosseously.

22. The method of claim 13, wherein the diameter of the gas nanobubbles is from 5 nm to 100 nm.

* * * * *